US008431129B2

(12) United States Patent
Hart et al.

(10) Patent No.: US 8,431,129 B2
(45) Date of Patent: Apr. 30, 2013

(54) METHOD OF TREATING FIBROPROLIFERATIVE DISORDERS OF THE HEART AND LUNG

(75) Inventors: Charles E. Hart, Woodinville, WA (US); Stavros Topouzis, Seattle, WA (US); Debra G. Gilbertson, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 13/619,228

(22) Filed: Sep. 14, 2012

(65) Prior Publication Data
US 2013/0022599 A1 Jan. 24, 2013

Related U.S. Application Data

(60) Division of application No. 12/780,809, filed on May 14, 2010, now Pat. No. 8,298,534, which is a continuation of application No. 11/539,271, filed on Oct. 6, 2006, now Pat. No. 7,722,870, which is a continuation of application No. 10/606,055, filed on Jun. 25, 2003, now Pat. No. 7,172,757, which is a division of application No. 09/808,972, filed on Mar. 14, 2001, now Pat. No. 6,630,142, which is a continuation-in-part of application No. 09/564,595, filed on May 3, 2000, now Pat. No. 6,495, 668.

(60) Provisional application No. 60/235,295, filed on Sep. 26, 2000, provisional application No. 60/180,169, filed on Feb. 4, 2000, provisional application No. 60/164,463, filed on Nov. 10, 1999, provisional application No. 60/132, 250, filed on May 3, 1999.

(51) Int. Cl.
*A61K 39/395* (2006.01)
*C12P 21/08* (2006.01)
*C07K 16/18* (2006.01)
*C07K 14/435* (2006.01)

(52) U.S. Cl.
USPC .................. 424/139.1; 424/133.1; 424/141.1; 424/135.1; 530/388.1; 530/350; 514/8.2

(58) Field of Classification Search .................. None
See application file for complete search history.

(56) References Cited

U.S. PATENT DOCUMENTS

| 5,238,950 | A | 8/1993 | Clader et al. |
|---|---|---|---|
| 5,700,823 | A | 12/1997 | Hirth et al. |
| 6,264,949 | B1 | 7/2001 | Friedman |
| 6,455,283 | B1 | 9/2002 | Ferrara et al. |
| 6,495,668 | B1 | 12/2002 | Gilbert et al. |
| 6,706,687 | B1 | 3/2004 | Eriksson et al. |
| 2002/0094546 | A1 | 7/2002 | Shimkets et al. |
| 2003/0049816 | A1 | 3/2003 | Baker et al. |
| 2004/0242850 | A1 | 12/2004 | Gilbert et al. |

FOREIGN PATENT DOCUMENTS

| EP | 0585242 B1 | 3/1994 |
|---|---|---|
| WO | 00/27879 A1 | 5/2000 |
| WO | 00/34474 A2 | 6/2000 |
| WO | 00/59940 A2 | 10/2000 |
| WO | 00/66736 A1 | 11/2000 |
| WO | 01/00878 A2 | 1/2001 |
| WO | 01/40466 A2 | 6/2001 |
| WO | 01/55430 A1 | 8/2001 |
| WO | 02/058716 A2 | 8/2002 |

OTHER PUBLICATIONS

Li et al., Diabetes, 2005; 54: 2227-2234.*
Rangel-Moreno et al., J Clin Invest. 2006; 116(12):3183-3194.*
Yu, L. et al., "Therapeutic strategies to halt renal fibrosis," Curr. Opin. Pharmacol., vol. 2(2):177-181 (2002).
Bergsten, E. et al., "PDGF-D is a specific, protease-activated ligand for the PDGF beta-receptor," Nat. Cell. Biol., vol. 3(5):512-516 (2001).
Bessho, K. et al., "Couteractive effects of HGF on PDGF-induced mesangial cell proliferation in a rat model of glomerulonephritis," Am. J. Physiol. Renal Physiol., vol. 284(6):F1171-F1180 (2003).
Bonfil, R.D. et al., "Proteases, growth factors, chemokines, and the microenvironment in prostate cancer bone metastasis," Urol. Oncol., vol. 25(5):407-411 (2007).
Boor, P. et al., "PDGF-D inhibition by CR002 ameliorates tubulointerstitial fibrosis following experimental glomerulonephritis," Nephrol. Dial. Transplant, vol. 22(5):1323-1331 (2007).
Booy, E.P. et al., "Monoclonal and bispecific antibodies as novel therapeutics," Arch. Immunol. Ther. Exp., vol. 54 (2):85-101 (2006).
Brady, L.M. et al., "Polyenylphosphatidylcholine inhibits PDGF-induced proliferation in rat hepatic stellate cells," Biochem. Biophys. Res. Commun., vol. 248(1):174-179 (1998).
Buchanan, Grant et al., "PC-3 Cells With Enhanced Androgen Receptor Signaling: A Model for Clonal Selection in Prostate Cancer," The Prostate, vol. 60:352-366 (2004).
Coppo, R. et al., "New perspectives in treatment of glomerulonephritis," Pediatr. Nephrol., vol. 19(3):256-265 (2004).
Deuel, T.F. et al., "Growth factors in fibrotic diseases," N. Engl. J. Med., vol. 317(4):236-237 (1987).
Eddy, A.A., "Molecular basis of renal fibrosis," Pediatr. Nephrol., vol. 15(3-4):290-301 (2000).
Eitner, F. et al., "Therapeutic targets for prevention and regression of progressive fibrosing renal diseases," Curr. Opin. Investig. Drugs, vol. 6(3):255-261 (2005).

(Continued)

*Primary Examiner* — Bridget E Bunner
*Assistant Examiner* — Christina Borgeest
(74) *Attorney, Agent, or Firm* — Nelson Mullins Riley & Scarborough LLP; Jane E. Remillard, Esq.; Jeanne M. DiGiorgio

(57) ABSTRACT

Materials and Methods for reducing cell proliferation or extracellular matrix production in a mammal are disclosed. The methods comprise administering to a mammal a composition comprising a therapeutically effective amount of a zvegf4 antagonist in combination with a pharmaceutically acceptable delivery vehicle. Exemplary zvegf4 antagonists include anti-zvegf4 antibodies, inhibitory polynucleotides, inhibitors of zvegf4 activation, and mitogenically inactive, receptor-binding variants of zvegf4. The materials and methods are useful in the treatment of, inter alia, fibroproliferative disorders of the kidney, liver, and bone.

6 Claims, 7 Drawing Sheets

OTHER PUBLICATIONS

Figure 1A:
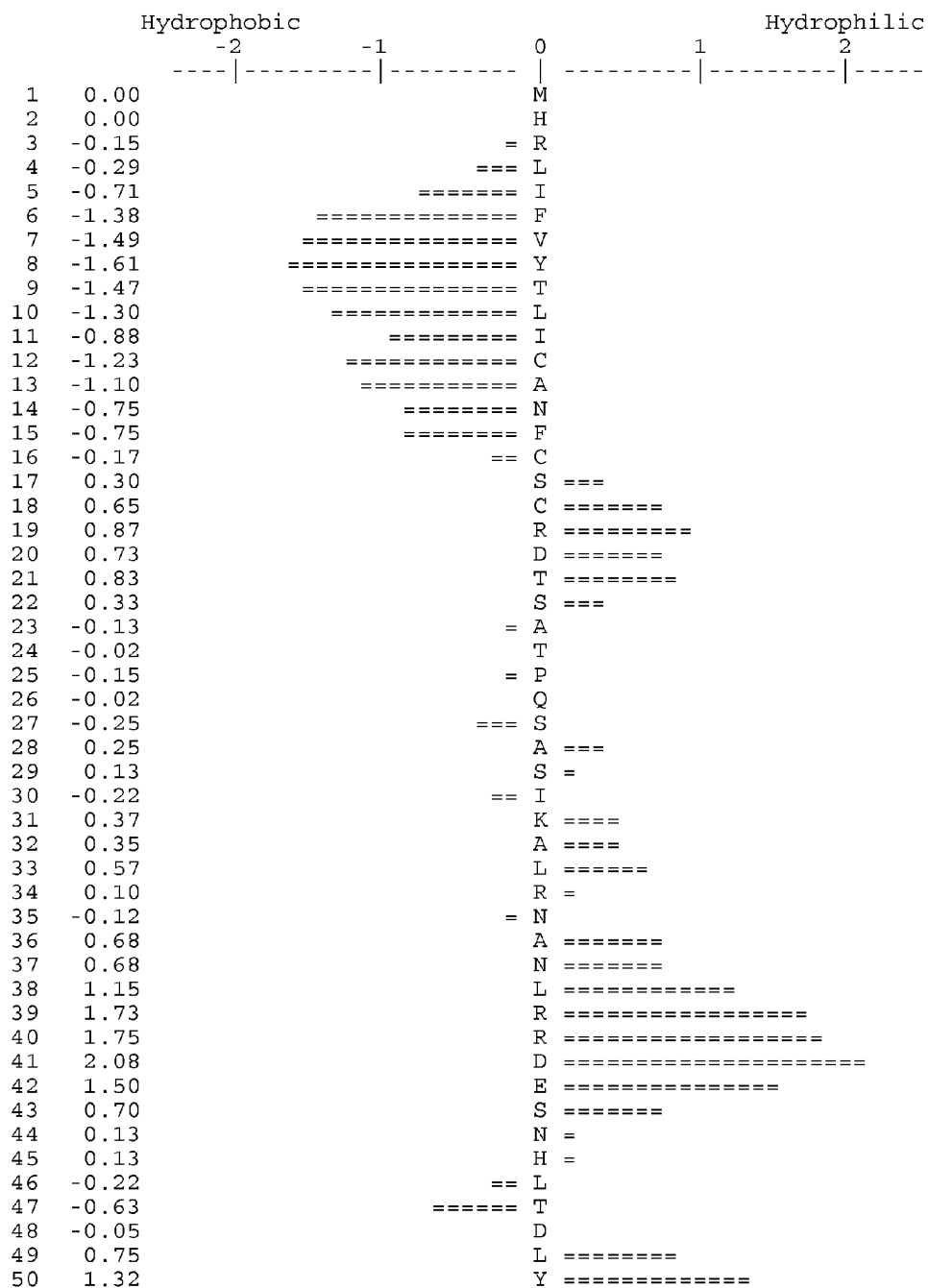

Ellsworth et al., from Cancer Drug Discovery and Development: The Oncogenomics Handbook, W.J. LaRochelle (Ed.), Humana Press, Inc., Totowa, NJ (2005).

Eng, E. et al., "Is mesangial cell proliferation required for extracellular matrix expansion in glomerular disease?" Contrib. Nephrol., vol. 107:156-162 (1994).

Floege, J. et al., "Infusion of platelet-derived growth factor or basic fibroblast growth factor induces selective glomerular mesangial cell proliferation and matrix accumulation in rats," J. Clin. Invest., vol. 92(6):2952-2962 (1993).

Friedman, S.L., "Cytokines and fibrogenesis," Semin. Liver Dis., vol. 19(2):129-140 (1999).

Glomerulonephritis: Definition and Much More from Answers.com, 3 pages, (2006).

Griffiths, A.D. et al., "Strategies for selection of antibodies by phage display," Curr. Opin. Biotechnol., vol. 9 (1):102-108 (1998).

Hamada, T. et al., "Molecular cloning of SCDGF-B, a novel growth factor homologous to SCDGF/PDGF-C/fallotein," Biochem. Biophys. Res. Commun., vol. 280(3):733-737 (2001).

Heldin, C.H. et al., "Mechanism of action and in vivo role of platelet-derived growth factor," Physiol. Rev., vol. 79 (4):1283-1316 (1999).

Herceptin trastuzumab, "Who is Herceptin for?" http://www.herceptin.com, 3 pages (2011).

Hudkins, K.L. et al., "Exogenous PDGF-D is a potent mesangial cell mitogen and causes a severe mesangial proliferative glomerulopathy," J. Am. Soc. Nephrol., vol. 15(2):286-298 (2004).

Iredale, J.P. et al., "Mechanisms of spontaneous resolution of rat liver fibrosis. Hepatic stellate cell apoptosis and reduced hepatic expression of metalloproteinase inhibitors," J. Clin. Invest., vol. 102(3):538-549 (1998).

Isaka, Y. et al., "Glomerulosclerosis induced by in vivo transfection of transforming growth factor-beta or platelet-derived growth factor gene into the rat kidney," J. Clin. Invest., vol. 92(6):2597-2601 (1993).

Isbrucker, R.A. et al., "Platelet-derived growth factor adn pentoxifylline modulation of collagen synthesis in myofibroblasts," Toxicol. Appl. PHarmacol., vol. 149(1):120-126 (1998).

Johnson, R.J. et al., "Inhibition of mesangial cell proliferation and matrix expansion in glomerulonephritis in the rat by antibody to platelet-derived growth factor," J. Exp. Med., vol. 175(5):1413-1416 (1992).

Kallio, E.A. et al., "Role of platelet-derived growth factor in obliterative bronchiolitis (chronic rejection) in the rat," Am. J. Respir. Crit. Care Med., vol. 160(4):1324-1332 (1999).

Larochelle, W.J. et al., "PDGF-D, a new protease-activated growth factor," Nat. Cell. Biol., vol. 3(5):517-521 (2001).

Li, D. et al., "Liver fibrogenesis and the role of hepatic stellate cells: new insights and prospects for therapy," J. Gastroenterol. Hepatol., vol. 14(7):618-633 (1999).

Mann, D.A. et al., "Transcriptional regulation of hepatic stellate cell activation," Gut, vol. 50(6):891-896 (2002).

Martinet, Y. et al., "Exaggerated spontaneous release of platelet-derived growth factor by alveolar macrophages from patients with idiopathic pulmonary fibrosis," N. Engl. J. Med., vol. 317(4):202-209 (1987).

Ostendorf, T. et al., "A fully human monoclonal antibody (CR002) identifies PDGF-D as a novel mediator of mesangioproliferative glomerulonephritis," J. Am. Soc. Nephrol., vol. 14(9):2237-2247 (2003).

Ostendorf, T. et al., "Antagonism of PDGF-D by human antibody CR002 prevents renal scarring in experimental glomerulonephritis," J. Am. Soc. Nephrol., vol. 17(4):1054-1062 (2006).

Papalas, John A. et al., "Osteosarcoma after radiotherapy for prostate cancer," Annals of Diagnostic Pathology, vol. 15(3):194-197 (2011).

Pinzani, M. et al., "Inhibition by pentoxifylline of extracellular signal-regulated kinase activation by platelet-derived growth factor in hepatic stellate cells," Br. J. Pharmacol., vol. 119(6):1117-1124 (1996).

Powell, D.W. et al., "Myofibroblasts. I. Paracrine cells important in health and disease," Am. J. Physiol., vol. 277(1 pt. 1):C1-C9 (1999).

Preaux, A.M. et al., "Pentoxifylline inhibits growth and collagen synthesis of cultured human hepatic myofibroblast-like cells," Hepatology, vol. 26(2):315-322 (1997).

Reigstad, L.J. et al., "Structural and functional specificities of PDGF-C and PDGF-D, the novel member of the platelet-derived growth factors family," FEBS J., vol. 272(22):5723-5741 (2005).

Rice, A.B. et al., "Specific inhibitors of platelet-derived growth factor or epidermal growth factor receptor tyrosine kinase reduce pulmonary fibrosis in rats," Am. J. Pathol., vol. 155(1):213-221 (1999).

Smits, A. et al., "Expression of platelet-derived growth factor and its receptors in proliferative disorders of fibroblastic origin," Am. J. Pathol., vol. 140(3):639-648 (1992).

Song, Lynda Li et al., "Cancer stem cells—an old idea that's new again: implications for the diagnosis and treatment of breast cancer," Expert Opin. Biol. Ther., vol. 7(4):431-438 (2007).

Taneda, S. et al., "Obstructive uropathy in mice and humans: potential role for PDGF-D in the progression of tubulointerstitial injury," J. Am. Soc. Nephrol., vol. 14(10):2544-2555 (2003).

Tannock, Ian F. et al., The Basic Science of Oncology, Third Edition, McGraw-Hill, New York, pp. 357-358 (1998).

Thompson, Deborah L. et al., "The Derivation and Characterization of Stromal Cell Lines from the Bone Marrow of p53-/- Mice: New Insights into Osteoblast and Adipocyte Differentiation," Journal of Bone and Mineral Research, vol. 13(2):195-204 (1998).

Tsai, Y.J. et al., "Identification of a novel platelet-derived growth factor-like gene, fallotein, in the human reproductive tract," Biochim. Biophyis Acta, vol. 1492 (1):196-202 (2000).

Ustach, Carolyn V. et al., "Platelet-Derived Growth Factor D Is Activated by Urokinase Plasminogen Activator in Prostate Carcinoma Cells," Molecular and Cellular Biology, vol. 25(14):6279-6288 (2005).

Uutela, M. et al., "Chromosomal location, exon structure, and vascular expression patterns of the human PDGFC and PDGFD genes," Circulation, vol. 103(18):2242-2247 (2001).

Wang, Zhiwei et al., "PDGF-D Signaling: A Novel Target in Cancer Therapy," Current Drug Targets, vol. 10:38-41 (2009).

Yagi, M. et al., "Beneficial effects of a novel inhibitor of platelet-derived growth factor receptor autophosphorylation in the rat with mesangial proliferative glomerulonephritis," Gen. Pharmacol., vol. 31(5):765-773 (1998).

Yi, E.S. et al., "Platelet-derived growth factor causes pulmonary cell proliferation and collagen deposition in vivo," Am. J. Pathol., vol. 149(2):539-548 (1996).

Yoshida, M. et al., "In vivo gene transfer of an extracellular domain of platelet-derived growth factor beta receptor by the HVJ-liposome method ameliorates bleomycin-induced pulmonary fibrosis," Biochem. Biophys. Res. Commun., vol. 265(2):503-508 (1999).

* cited by examiner

METHOD OF TREATING FIBROPROLIFERATIVE DISORDERS OF THE HEART AND LUNG

CROSS-REFERENCE TO RELATED APPLICATIONS

This application is a division of U.S. application Ser. No. 12/780,809, filed May 14, 2010, now U.S. Pat. No. 8,298,534, which is a continuation of U.S. application Ser. No. 11/539, 271, filed Oct. 6, 2006, now U.S. Pat. No. 7,722,870, which is a continuation of U.S. application Ser. No. 10/606,055, filed Jun. 25, 2003, now U.S. Pat. No. 7,172,757, which is a division of U.S. application Ser. No. 09/808,972, filed Mar. 14, 2001, now U.S. Pat. No. 6,630,142, which claims the benefit of provisional application Ser. No. 60/235,295, filed Sep. 26, 2000, and which is a continuation-in-part of application Ser. No. 09/564,595, filed May 3, 2000, now U.S. Pat. No. 6,495, 668, which claims the benefit of provisional application Ser. Nos. 60/132,250, filed May 3, 1999, Ser. No. 60/164,463, filed Nov. 10, 1999, Ser. No. 60/180,169, filed Feb. 4, 2000. The contents of the aforementioned applications are hereby incorporated by reference.

BACKGROUND OF THE INVENTION

Fibroproliferative disorders are characterized by the abnormal accumulation of fibrous tissue ("fibrosis") that can occur as a part of the wound-healing process in damaged tissue. Such tissue damage may result from physical injury, inflammation, infection, exposure to toxins, and other causes. The fibroproliferative condition includes both a cell growth component and an extensive phase characterized by extracellular matrix accumulation. Examples of fibroproliferative disorders include dermal scar formation, keloids, liver fibrosis, lung fibrosis (e.g., silicosis, asbestosis), kidney fibrosis (including diabetic nephropathy), and glomerulosclerosis.

A variety of renal diseases can be classified as fibroproliferative. Glomerular (usually mesangial) cell proliferation occurs in many types of glomerulonephritides in conjunction with increased extracellular matrix accumulation (Iida et al., *Proc. Natl. Acad. Sci. USA* 88:6560-6564, 1991). For example, mesangial cell proliferation precedes glomerulosclerosis in the remnant kidney model (Floege et al., *Kidney International* 41:297-309, 1992), and experimental overexpression of growth factors such as PDGF-B and TGF-beta in the kidney induces cell proliferation, matrix accumulation, and glomerulosclerosis (Isaka et al., *J. Clin. Invest.* 92:2597-2601, 1993; Cybulsky, *Curr. Opin. Nephropathy and Hypert.* 9:217-223, 2000).

A number of vascular pathologies result from a combination of mesenchymal cell proliferation (smooth muscle and fibroblast-like) and extensive accumulation of extracellular matrix components. Such artery wall diseases as arteriosclerotic lesions, arteritis of various origins, and the vascular re-stenotic lesions that frequently follow angioplasty (Riessen et al., *Am. Heart J.* 135:357-364, 1998; Plenz et al., *Arterioscler. Thromb. Vasc. Biol.* 17:2489-2499, 1997; McCaffrey, *Cytokine Growth Factor Rev.* 11:103-114, 2000) are considered fibroproliferative. Other fibroproliferative responses include the fiborproliferative responses that occur in organs following transplant (e.g., heart transplants), at sites of vascular anastamosis, and at areas around catheter placements (e.g., arterio-venous shunts used for dialysis).

Bone formation, both physiologic and pathologic, can be described as the interplay between bone formation that results from proliferation of osteoblasts and production by them of extracellular matrix, and the replication of osteoclasts and their modulation of this matrix. Diseases where there is aberrant and ectopic bone formation, such as that occurring with prostate tumor metastases to the axial skeleton, are commonly characterized by active proliferation of the major cell types participating in bone formation as well as by elaboration by them of a complex bone matrix. These diseases can therefore be viewed as fibroproliferative.

Pulmonary fibrosis is a major cause of morbidity and mortality. Pulmonary fibrosis is associated with the use of high-dose antineoplastic agents (e.g., bleomycin) in chemotherapy and with bone marrow transplantation for cancer treatment. The development of lung disease is the major dose-limiting side effect of bleomycin. See, Tran et al., *J. Clin. Invest.* 99:608-617, 1997. Idiopathic pulmonary fibrosis (IPF) is another lung fibrotic disease characterized by a fibroproliferative response. Various factors, including aspiration and exposure to environmental pollutants may result in IPF (Egan, *The Lancet* 354:1839-1840, 1999). The standard treatment for IPF is oral glucocorticoids. However, lung function improves in less than 30 percent of patients who receive this treatment, and, regardless of treatment, the median survival is four to five years after the onset of symptoms. The proliferation of fibroblasts and the accumulation of interstitial collagens are the hallmarks of progressive organ fibrosis, however the biochemical mechanism of induction of lung fibrosis remains unclear (Ziesche et al., *New Eng. J. Med.* 341:1264-1269, 1999; Kuwano et al., *J. Clin Invest.* 104:13-19, 1999). Pulmonary hypertension results from a variety of initiating stimuli. Its progression is associated with pulmonary vascular sclerosis, which includes abnormal endothelial morphology and function, muscularization of normally nonmuscular peripheral arteries related to differentiation of pericytes, and medial hypertrophy and neointimal formation in muscular arteries as a consequence of hypertrophy, proliferation, and migration of resident smooth muscle cells and increased production of extracellular matrix components. These components include collagen, elastin, fibronectin, and tenascin-C. This fibroproliferative response can progress to life-threatening pulmonary arterial obstructive disease (Cowan et al., *J. Clin. Invest.* 105:21-34, 2000).

Liver (hepatic) fibrosis occurs as a part of the wound-healing response to chronic liver injury. Fibrosis occurs as a complication of haemochromatosis, Wilson's disease, alcoholism, schistosomiasis, viral hepatitis, bile duct obstruction, toxin exposure, and matabolic disorders. This formation of scar tissue is believed to represent an attempt by the body to encapsulate the injured tissue. Liver fibrosis is characterized by the accumulation of extracellular matrix that can be distinguished qualitatively from that in normal liver. Left unchecked, hepatic fibrosis progresses to cirrhosis (defined by the presence of encapsulated nodules), liver failure, and death.

In recent years there have been significant advances in the understanding of the cellular and biochemical mechanisms underlying liver fibrosis (reviewed by Li and Friedman, *J. Gastroenterol. Hepatol.* 14:618-633, 1999). Stellate (Ito) cells are believed to be a major source of extracellular matrix in the liver. Stellate cells respond to a variety of cytokines present in the liver, some of which they also produce (Friedman, *Seminars in Liver Disease* 19:129-140, 1999).

As summarized by Li and Friedman (ibid.), actual and proposed therapeutic strategies for liver fibrosis include removal of the underlying cause (e.g., toxin or infectious agent), suppression of inflammation (using, e.g., corticosteroids, IL-1 receptor antagonists, or other agents), down-regulation of stellate cell activation (using, e.g., gamma interferon or antioxidants), promotion of matrix degradation, or promotion of stellate cell apoptosis. Despite recent progress, many of these strategies are still in the experimental stage, and existing therapies are aimed at suppressing inflammation rather than addressing the underlying biochemical processes. Thus, there remains a need in the art for materials and methods for treating fibroproliferative disorders, including liver fibrosis.

DESCRIPTION OF THE INVENTION

Within one aspect of the present invention there is provided a method of reducing proliferation of or extracellular matrix production by a cell in a mammal comprising administering to the mammal a composition comprising a therapeutically effective amount of a zvegf4 antagonist in combination with a pharmaceutically acceptable delivery vehicle, wherein the zvegf4 antagonist is selected from the group consisting of anti-zvegf4 antibodies, inhibitory polynucleotides, inhibitors of zvegf4 activation, and mitogenically inactive, receptor-binding variants of zvegf4. Within certain embodiments of the invention the proliferation of mesangial, epithelial, endothelial, smooth muscle, fibroblast, osteoblast, osteoclast, neuronal, stromal, stellate, or interstitial cells is reduced. Within another embodiment of the invention the proliferation of tumor cells, such as prostate tumor cells, is reduced. Within another embodiment of the invention extracellular matrix production is reduced. Within other embodiments of the invention the mammal is suffering from a fibroproliferative disorder of the kidney, liver, or bone.

Within a related aspect of the invention there is provided a method of reducing proliferation of or extracellular matrix production by a cell in a mammal, wherein the cell is an epithelial, endothelial, smooth muscle, fibroblast, osteoblast, neuronal, or stellate cell, the method comprising administering to the mammal a composition comprising a therapeutically effective amount of a zvegf4 antagonist in combination with a pharmaceutically acceptable delivery vehicle, wherein the zvegf4 antagonist is selected from the group consisting of anti-zvegf4 antibodies, inhibitory polynucleotides, inhibitors of zvegf4 activation, and mitogenically inactive, receptor-binding variants of zvegf4.

Within a further aspect of the invention there is provided a method of reducing proliferation of or extracellular matrix production by prostate tumor cells in a mammal, the method comprising administering to the mammal a composition comprising a therapeutically effective amount of a zvegf4 antagonist in combination with a pharmaceutically acceptable delivery vehicle, wherein the zvegf4 antagonist is selected from the group consisting of anti-zvegf4 antibodies, inhibitory polynucleotides, inhibitors of zvegf4 activation, and mitogenically inactive, receptor-binding variants of zvegf4.

Within another aspect of the invention there is provided a method of reducing metastasis of prostate cancer cells to bone in a mammal, the method comprising administering to the mammal a composition comprising a therapeutically effective amount of a zvegf4 antagonist in combination with a pharmaceutically acceptable delivery vehicle, wherein the zvegf4 antagonist is selected from the group consisting of anti-zvegf4 antibodies, inhibitory polynucleotides, inhibitors of zvegf4 activation, and mitogenically inactive, receptor-binding variants of zvegf4.

Within a further aspect of the invention there is provided a method of treating a fibroproliferative disorder in a mammal comprising administering to the mammal a composition comprising a therapeutically effective amount of a zvegf4 antagonist in combination with a pharmaceutically acceptable delivery vehicle, wherein the zvegf4 antagonist is selected from the group consisting of anti-zvegf4 antibodies, inhibitors of zvegf4 activation, mitogenically inactive receptor-binding zvegf4 variant polypeptides, and inhibitory polynucleotides. Within certain embodiments of the invention the fibroproliferative disorder is a fibroproliferative disorder of liver, kidney, or bone.

Within an additional aspect of the invention there is provided a method of reducing stellate cell activation in a mammal comprising administering to the mammal a composition comprising a zvegf4 antagonist in combination with a pharmaceutically acceptable delivery vehicle, wherein the zvegf4 antagonist is selected from the group consisting of anti-zvegf4 antibodies, mitogenically inactive receptor-binding zvegf4 variant polypeptides, and inhibitory polynucleotides, in an amount sufficient to reduce stellate cell activation.

Within certain embodiments of the above-disclosed methods, the zvegf4 antagonist is selected from the group consisting of anti-zvegf4 antibodies and inhibitory polynucleotides. Within other embodiments, the zvegf4 antagonist is an anti-zvegf4 antibody. Within additional embodiments of these methods, the zvegf4 antagonist is administered in combination with an antagonist of a second growth factor.

These and other aspects of the invention will become evident upon reference to the following detailed description of the invention and the accompanying FIGURE.

Figure 1B:
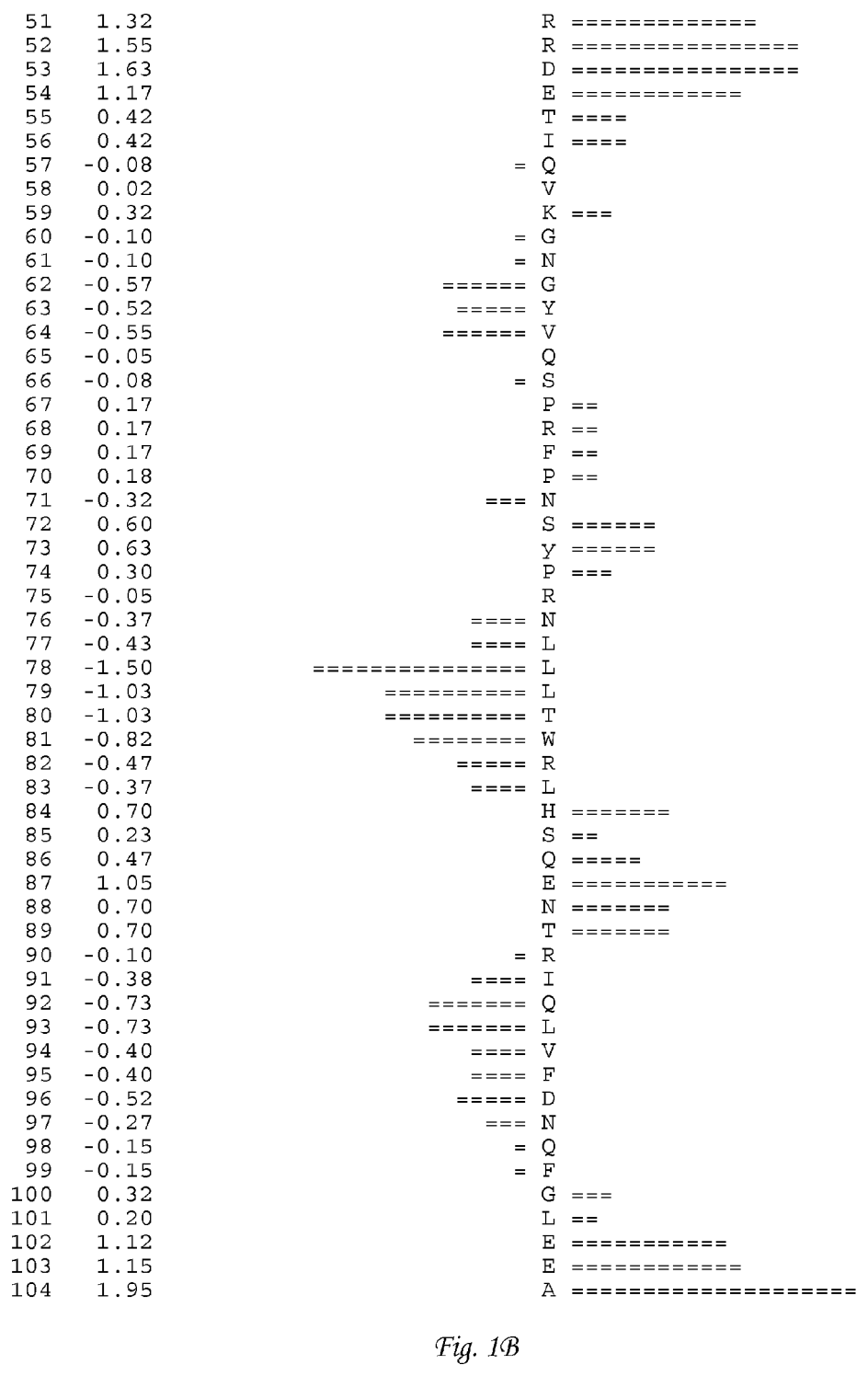
Figure 1C:
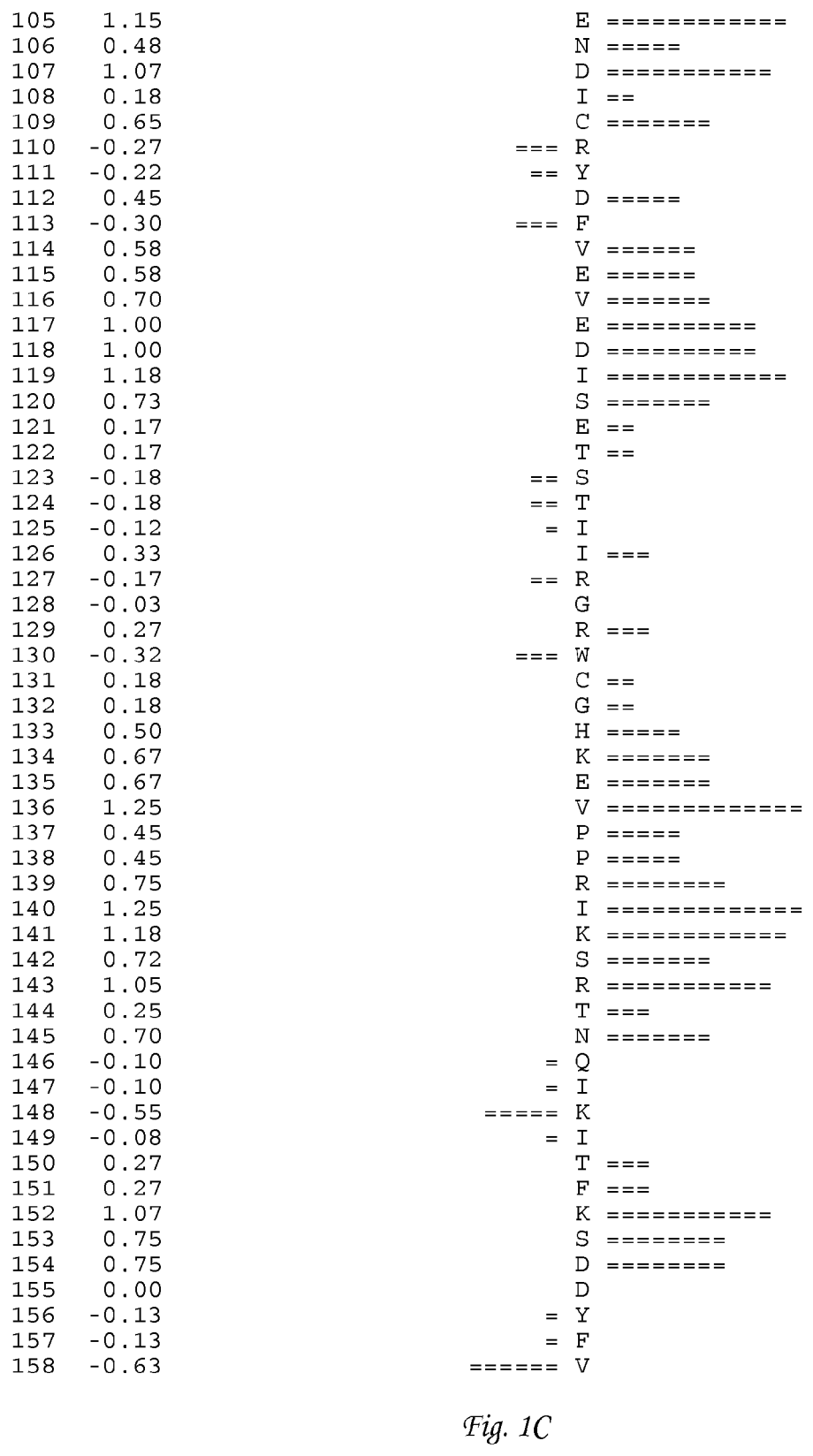
Figure 1D:
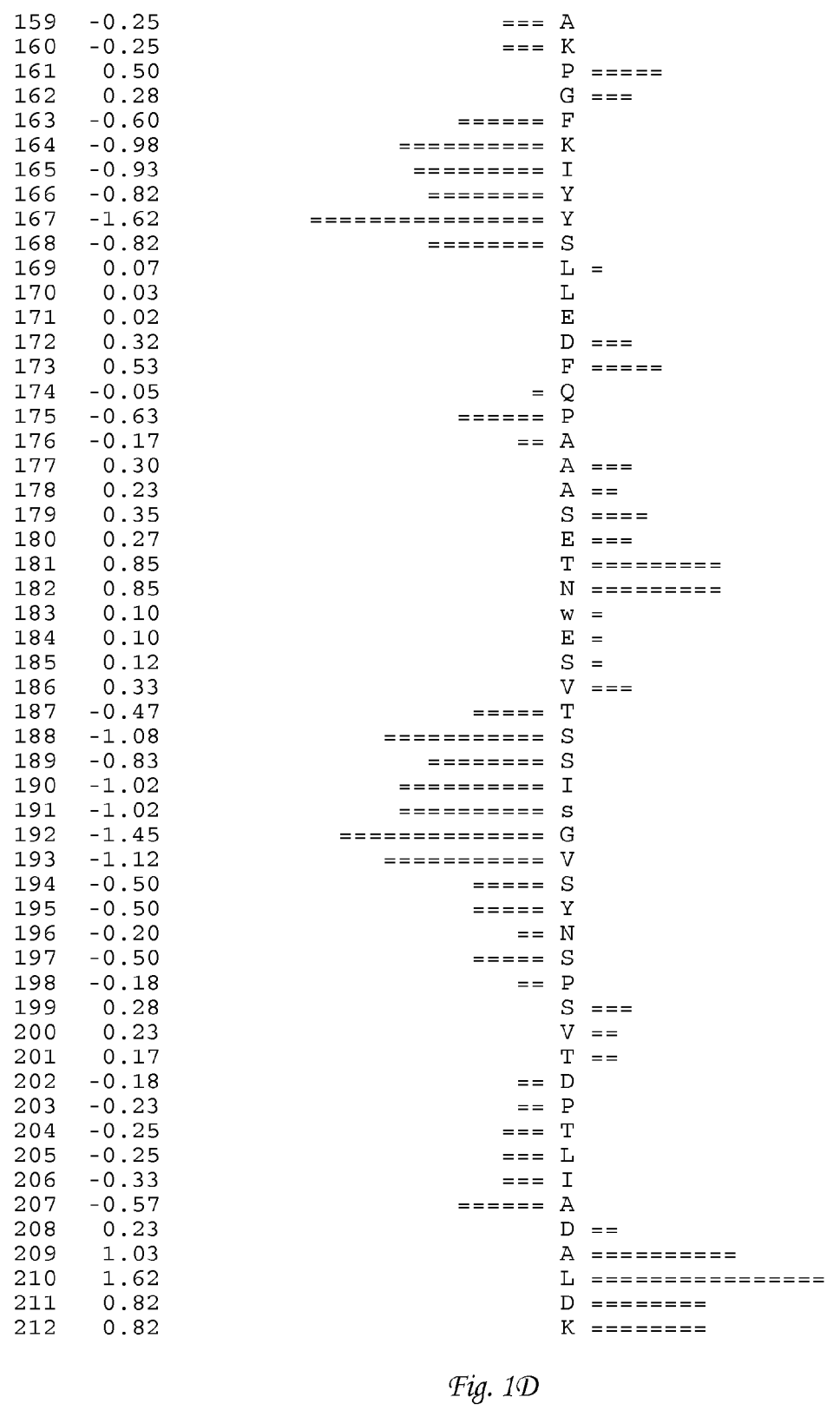
Figure 1E:
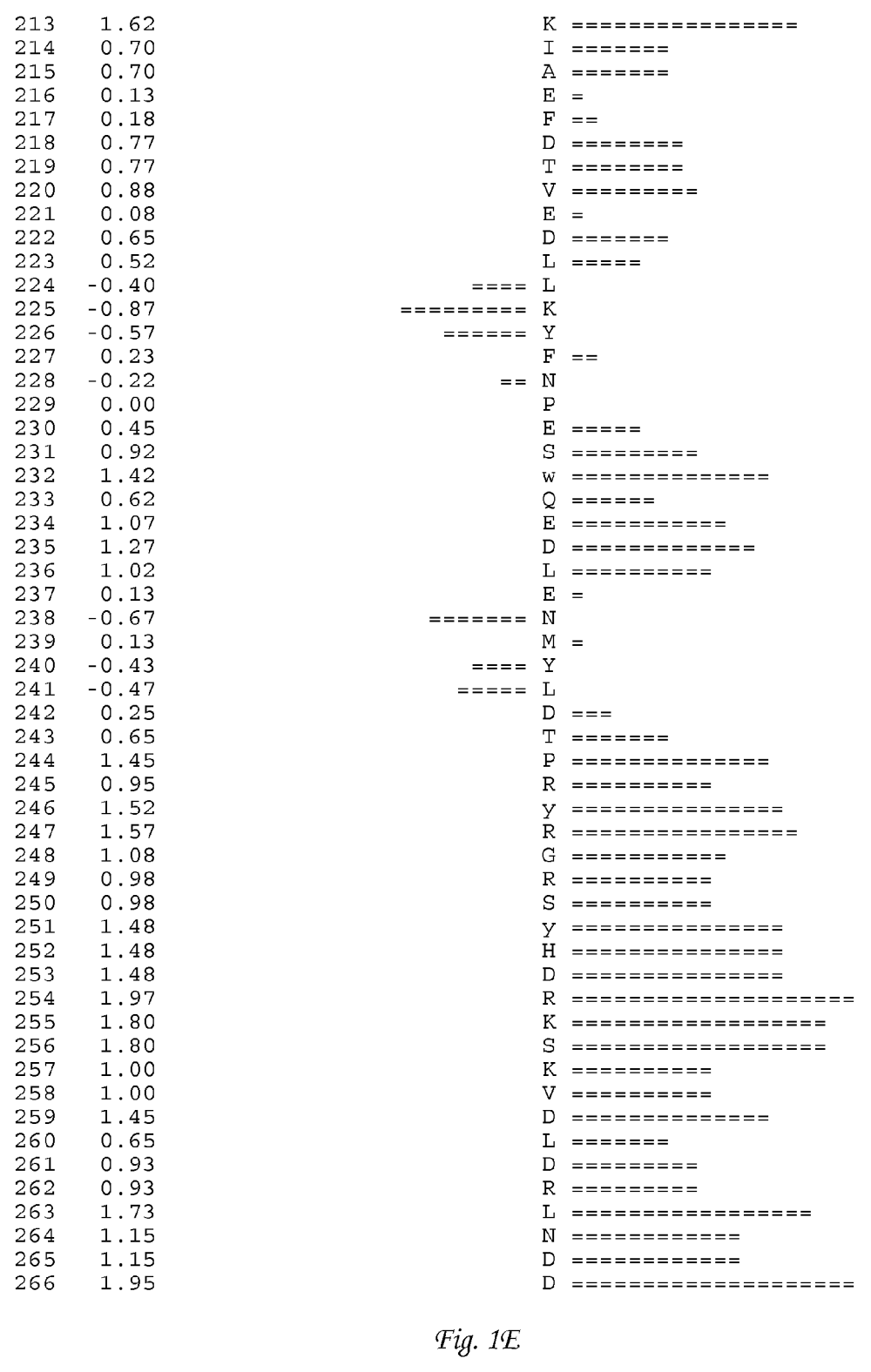
Figure 1F:
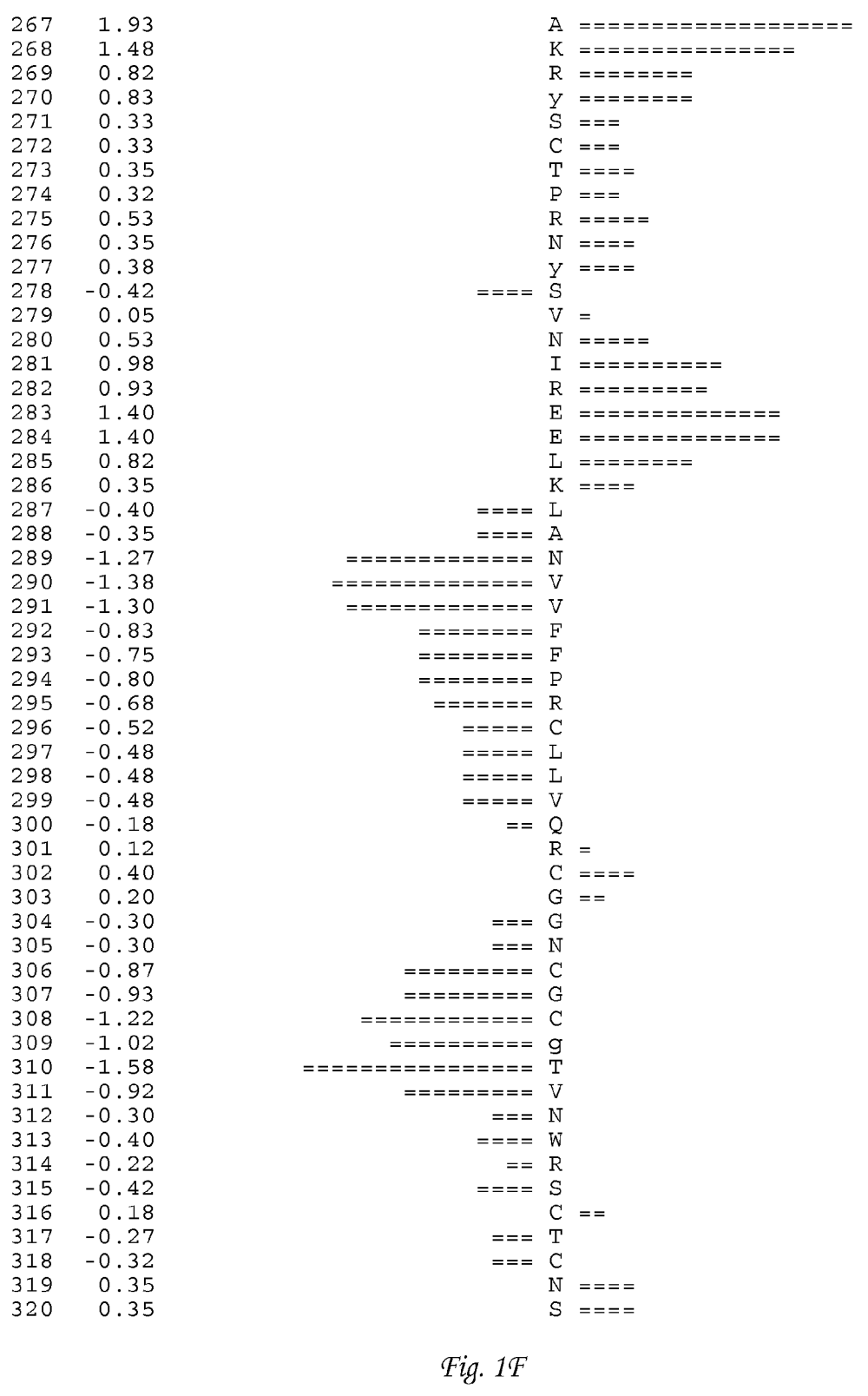
Figure 1G:
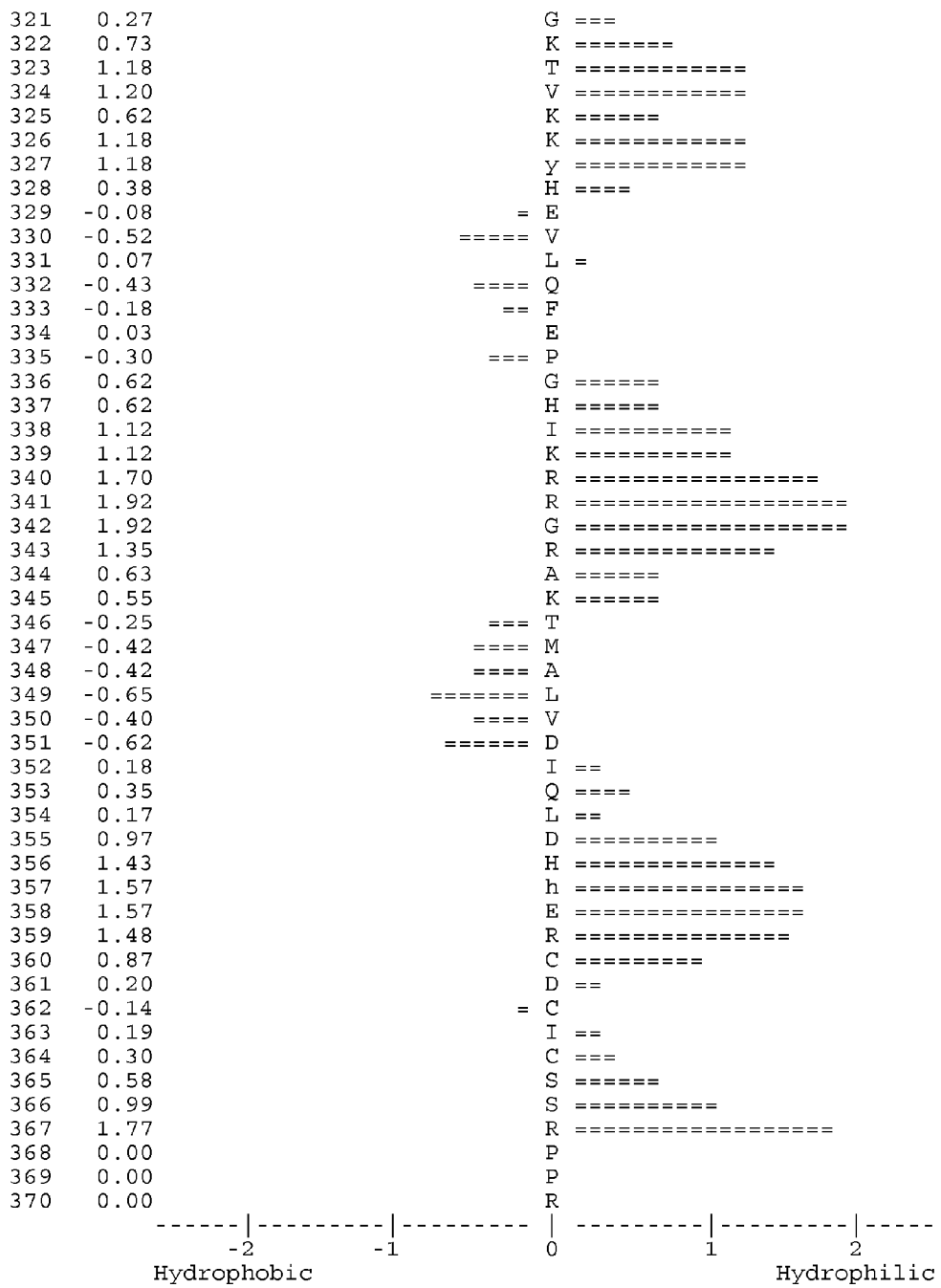

FIGS. 1A-1G are a Hopp/Woods hydrophilicity profile of the amino acid sequence shown in SEQ ID NO:2. The profile is based on a sliding six-residue window. Buried G, S, and T residues and exposed H, Y, and W residues were ignored. These residues are indicated in the FIGURE by lower case letters.

The term "antagonist" is used herein to denote a compound that reduces a biological activity of another compound. Within the present invention, a "zvegf4 antagonist" is a compound that reduces the receptor-mediated biological activity (e.g., mitogenic activity) of zvegf4 on a target cell. Antagonists may exert their action by competing with zvegf4 for binding sites on a cell-surface receptor, by binding to zvegf4 and preventing it from binding to a cell-surface receptor, by otherwise interfering with receptor function, by reducing production of zvegf4, or by other means.

"Extracellular matrix" (ECM) is a complex mixture of macromolecules that accumulates within tissues in close apposition to cell surfaces. ECM contains secreted macromolecules such as collagens I, III and IV; fibronectin; laminins; and various proteoglycans. These macromolecules can be organized to provide cohesion to the tissue and can contribute to its structural and mechanical properties. ECM can act as a depository for, and release site of potent secreted growth factors, and is known to influence growth, survival and differentiation of the cells it surrounds. Pathologic ECM accumulation, if unchecked, can restrict access of nutrients, growth factors, and other physiologically important molecules to cells and can lead to the creation of areas of low live cell density. Over time, this accumulation can result in the inability of a tissue to perform its specific metabolic and structural roles, and may ultimately lead to overt cell and tissue death.

An "inhibitory polynucleotide" is a DNA or RNA molecule that reduces or prevents expression (transcription or translation) of a second (target) polynucleotide. Inhibitory polynucleotides include antisense polynucleotides, ribozymes, and external guide sequences. The term "inhibitory polynucleotide" further includes DNA and RNA molecules that encode the actual inhibitory species, such as DNA molecules that encode ribozymes.

The terms "treat" and "treatment" are used broadly to denote therapeutic and prophylactic interventions that favorably alter a pathological state. Treatments include procedures that moderate or reverse the progression of, reduce the severity of prevent, or cure a disease.

The term "zvegf4 protein" is used herein to denote proteins comprising the growth factor domain of a zvegf4 polypeptide (e.g., residues 258-370 of human zvegf4 (SEQ ID NO:2) or mouse zvegf4 (SEQ ID NO:4)), wherein the protein is mitogenic for cells expressing cell-surface PDGF α- and/or β-receptor subunit. Zvegf4 has been found to activate the αα, αβ, and ββ isoforms of PDGF receptor. Zvegf4 proteins include homodimers and heterodimers as disclosed below. Using methods known in the art, zvegf4 proteins can be prepared in a variety of foams, including glycosylated or non-glycosylated, pegylated or non-pegylated, with or without an initial methionine residue, and as fusion proteins as disclosed in more detail below.

All references cited herein are incorporated by reference in their entirety.

The present invention provides methods for reducing proliferation of or extracellular matrix production by a cell in a mammal using zvegf4 antagonists. The invention further provides methods of treating fibroproliferative disorders in a mammal using zvegf4 antagonists. Zvegf4 is a multi-domain protein that is structurally related to platelet-derived growth factor (PDGF) and the vascular endothelial growth factors (VEGF). This protein is also referred to as "PDGF-D" (WIPO Publication WO 00/27879).

Structural predictions based on the zvegf4 sequence and its homology to other growth factors suggests that the polypeptide can form homomultimers or heteromultimers that act on tissues by modulating cell proliferation, migration, differentiation, or metabolism. Experimental evidence supports these predictions. Zvegf4 heteromultimers may comprise a polypeptide from another member of the PDGF/VEGF family of proteins, including VEGF, VEGF-B, VEGF-C, VEGF-D, zvegf3/PDGF-C (WO 00/34474), PlGF (Maglione et al., *Proc. Natl. Acad. Sci. USA* 88:9267-9271, 1991), PDGF-A (Murray et al., U.S. Pat. No. 4,899,919; Heldin et al., U.S. Pat. No. 5,219,759), or PDGF-B (Chiu et al., *Cell* 37:123-129, 1984; Johnsson et al., *EMBO J.* 3:921-928, 1984).

The zvegf4 polypeptide chain comprises a growth factor domain, a CUB domain, and an interdomain region linking the CUB and growth factor domains. The growth factor domain is characterized by an arrangement of cysteine residues and beta strands that is characteristic of the "cystine knot" structure of the PDGF family. The CUB domain shows sequence homology to CUB domains in the neuropilins (Takagi et al., *Neuron* 7:295-307, 1991; Soker et al., *Cell* 92:735-745, 1998), human bone morphogenetic protein-1 (Wozney et al., *Science* 242: 1528-1534, 1988), porcine seminal plasma protein and bovine acidic seminal fluid protein (Romero et al., *Nat. Struct. Biol.* 4:783-788, 1997), and *X. laevis* tolloid-like protein (Lin et al., *Dev. Growth Differ.* 39:43-51, 1997).

A representative human zvegf4 polypeptide sequence is shown in SEQ ID NO:2, and a representative mouse zvegf4 polypeptide sequence is shown in SEQ ID NO:4. DNAs encoding these polypeptides are shown in SEQ ID NOS:1 and 3, respectively. Analysis of the amino acid sequence shown in SEQ ID NO:2 indicates that residues 1 to 18 form a secretory peptide. The CUB domain extends from residue 52 to residue 179. A propeptide-like sequence extends from residue 180 to either residue 245, residue 249 or residue 257, and includes four potential cleavage sites at its carboxyl terminus, monobasic sites at residue 245 and residue 249, a dibasic site at residues 254-255, and a target site for furin or a furin-like protease at residues 254-257. Protein produced in a baculovirus expression system showed cleavage between residues 249 and 250, and included longer species with amino termini at residues 19 and 35. The growth factor domain extends from residue 258 to residue 370, and may include additional residues at the N-terminus (e.g., residues 250 to 257 or residues 246 to 257). Those skilled in the art will recognize that domain boundaries are somewhat imprecise and can be expected to vary by up to ±5 residues from the specified positions. Corresponding domains in mouse and other non-human zvegf4s can be determined by those of ordinary skill in the art from sequence alignments. Cleavage of full-length human zvegf4 with plasmin resulted in activation of the zvegf4 polypeptide as determined in a cellular assay using a PDGF receptor and luciferase reporter gene. By Western analysis, a band migrating at approximately the same size as the growth factor domain was observed in this preparation.

Signal peptide cleavage is predicted to occur in human zvegf4 after residue 18 (±3 residues). Upon comparison of human and mouse zvegf4 sequences, alternative signal peptide cleavage sites are predicted after residue 23 and/or residue 24. This analysis suggests that the zvegf4 polypeptide chain may be cleaved to produce a plurality of monomeric species, some of which are shown in Table 1. In certain host cells, cleavage after Lys-255 is expected to result in subsequent removal of residues 254-255, although polypeptides with a carboxyl terminus at residue 255 may also be prepared. Cleavage after Lys-257 is expected to result in subsequent removal of residue 257. These cleavage sites can be modified to prevent proteolysis and thus provide for the production of uncleaved zvegf4 polypeptides and multimers comprising them. Actual cleavage patterns are expected to vary among host cells.

TABLE 1

| Monomer | Residues (SEQ ID NO: 2) |
|---|---|
| CUB domain | 19-179 |
|  | 24-179 |
|  | 25-179 |
|  | 35-179 |
|  | 52-179 |
| CUB domain + | 19-257 |
| interdomain region | 24-257 |
|  | 25-257 |
|  | 35-257 |
|  | 52-257 |
|  | 19-255 |
|  | 24-255 |
|  | 25-255 |
|  | 35-255 |
|  | 52-255 |
|  | 19-253 |
|  | 24-253 |
|  | 25-253 |
|  | 35-253 |
|  | 52-253 |
|  | 19-249 |
|  | 24-249 |
|  | 25-249 |
|  | 35-249 |
|  | 52-249 |
|  | 19-245 |
|  | 24-245 |
|  | 25-245 |
|  | 35-245 |
|  | 52-245 |
| CUB domain + interdomain region + growth factor domain | 19-370 |
|  | 24-370 |
|  | 25-370 |
|  | 35-370 |
|  | 52-370 |

TABLE 1-continued

| Monomer | Residues (SEQ ID NO: 2) |
|---|---|
| Growth factor domain | 246-370 |
|  | 250-370 |
|  | 258-370 |
| Growth factor domain + interdomain region | 180-370 |

Zvegf4 can thus be prepared in a variety of multimeric forms comprising a zvegf4 polypeptide as disclosed above. These zvegf4 polypeptides include zvegf4$_{19\text{-}370}$, zvegf4$_{52\text{-}370}$, zvegf4$_{246\text{-}370}$, zvegf4$_{250\text{-}370}$, and zvegf4$_{258\text{-}370}$. Variants and derivatives of these polypeptides can also be prepared as disclosed herein.

Zvegf4 proteins can be prepared as fusion proteins comprising amino- or carboxyl-terminal extensions, such as an amino-terminal methionine residue, an affinity tag, or a targeting polypeptide. For example, a zvegf4 protein can be prepared as a fusion with an affinity tag to facilitate purification. In principal, any peptide or protein for which an antibody or other specific binding agent is available can be used as an affinity tag. Affinity tags include, for example, a polyhistidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952-4, 1985), substance P, FLAG peptide (Hopp et al., *Biotechnology* 6:1204-1210, 1988), streptavidin binding peptide, maltose binding protein (Guan et al., *Gene* 67:21-30, 1987), cellulose binding protein, thioredoxin, ubiquitin, T7 polymerase, or other antigenic epitope or binding domain. Fusion of zvegf4 to, for example, maltose binding protein or glutatione S transferase can be used to improve yield in bacterial expression systems. In these instances the non-zvegf4 portion of the fusion protein ordinarily will be removed prior to use. Separation of the zvegf4 and non-zvegf4 portions of the fusion protein is facilitated by providing a specific cleavage site between the two portions. Such methods are well known in the art. Zvegf4 can also be fused to a targeting peptide, such as an antibody (including polyclonal antibodies, monoclonal antibodies, antigen-binding fragments thereof such as F(ab')$_2$ and Fab fragments, single chain antibodies, and the like) or other peptidic moiety that binds to a target tissue.

Variations can be made in the zvegf4 amino acid sequences shown in SEQ ID NO:2 and SEQ ID NO:4 to provide inactive, receptor-binding polypeptides that act as zvegf4 antagonists. Such variations include amino acid substitutions, deletions, and insertions. While not wishing to be bound by theory, it is believed that residues within regions 273-295 and 307-317 of human zveg4 (SEQ ID NO:2) may be involved in ligand-receptor interactions. It is also believed that the CUB domain may mediate the binding of zvegf4 to certain cell-surface receptors, thereby providing a targeting function for delivery of the growth factor domain. The CUB domain, in the absence of an active growth factor domain, may therefore be useful as a zvegf4 antagonist. The effects of amino acid sequence changes at specific positions in zvegf4 proteins can be assessed using procedures known in the art, such as site-directed mutagenesis or alanine-scanning mutagenesis (Cunningham and Wells, *Science* 244, 1081-1085, 1989; Bass et al., *Proc. Natl. Acad. Sci. USA* 88:4498-4502, 1991). Multiple amino acid substitutions can be made and tested using known methods of mutagenesis and screening, such as those disclosed by Reidhaar-Olson and Sauer (*Science* 241:53-57, 1988) or Bowie and Sauer (*Proc. Natl. Acad. Sci. USA* 86:2152-2156, 1989). Other methods that can be used include phage display (e.g., Lowman et al., *Biochem.* 30:10832-10837, 1991; Ladner et al., U.S. Pat. No. 5,223,409; Huse, WIPO Publication WO 92/06204), region-directed mutagenesis (Derbyshire et al., *Gene* 46:145, 1986; Ner et al., *DNA* 7:127, 1988), and DNA shuffling (Stemmer, *Nature* 370:389-391, 1994; Stemmer, *Proc. Natl. Acad. Sci. USA* 91:10747-10751, 1994). The resultant mutant molecules are tested for receptor binding, mitogenic activity, or other properties (e.g., stimulation of extracellular matrix production) to identify amino acid residues that are critical to these functions. Mutagenesis can be combined with high-volume or high-throughput screening methods to detect biological activity of zvegf4 variant polypeptides, including biological activity in modulating cell proliferation. For example, mitogenesis assays that measure dye incorporation or $^3$H-thymidine incorporation can be carried out on large numbers of samples. Competition assays can be employed to confirm antagonist activity.

Zvegf4 proteins, including full-length proteins, variant proteins (including antagonists), biologically active fragments, and fusion proteins, can be produced in genetically engineered host cells according to conventional techniques. Suitable host cells are those cell types that can be transformed or transfected with exogenous DNA and grown in culture, and include bacteria, fungal cells, and cultured higher eukaryotic cells (including cultured cells of multicellular organisms). Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989, and Ausubel et al., eds., *Current Protocols in Molecular Biology*, Green and Wiley and Sons, NY, 1993. In general, a DNA sequence encoding a zvegf4 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors, and other elements is a matter of routine design within the level of ordinary skill in the art. Many such elements are described in the literature and are available through commercial suppliers. See, for example, WO 00/34474.

Zvegf4 proteins can comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, tert-leucine, norvaline, 2-azaphenylalanine, 3-azaphenylalanine, 4-azaphenylalanine, and 4-fluorophenylalanine Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259: 806-809, 1993; and Chung et al., *Proc. Natl. Acad. Sci. USA* 90:10145-10149, 1993). In a second method, translation is carried out in *Xenopus* oocytes by microinjection of mutated mRNA and chemically aminoacylated suppressor tRNAs (Turcatti et al., *J. Biol. Chem.* 271:19991-19998, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470-7476, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395-403, 1993).

Zvegf4 polypeptides or fragments thereof can also be prepared through chemical synthesis according to methods known in the art, including exclusive solid phase synthesis, partial solid phase methods, fragment condensation or classical solution synthesis. See, for example, Merrifield, *J. Am. Chem. Soc.* 85:2149, 1963; Stewart et al., *Solid Phase Peptide Synthesis* (2nd edition), Pierce Chemical Co., Rockford, Ill., 1984; Bayer and Rapp, *Chem. Pept. Prot.* 3:3, 1986; and Atherton et al., *Solid Phase Peptide Synthesis: A Practical Approach*, IRL Press, Oxford, 1989.

Zvegf4 proteins are purified by conventional protein purification methods, typically by a combination of chromatographic techniques. See, in general, *Affinity Chromatography: Principles & Methods*, Pharmacia LKB Biotechnology, Uppsala, Sweden, 1988; and Scopes, *Protein Purification: Principles and Practice*, Springer-Verlag, New York, 1994. Proteins comprising a polyhistidine affinity tag (typically about 6 histidine residues) are purified by affinity chromatography on a nickel chelate resin. See, for example, Houchuli et al., *Bio/Technol.* 6: 1321-1325, 1988. Proteins comprising a glu-glu tag can be purified by immunoaffinity chromatography according to conventional procedures. See, for example, Grussenmeyer et al., *Proc. Natl. Acad. Sci. USA* 82:7952-4, 1985. Maltose binding protein fusions are purified on an amylose column according to methods known in the art. Zvegf4 growth factor domain protein can be purified using a combination of chromatography on a strong cation exchanger followed by affinity chromatography and size-exclusion chromatography.

As shown in more detail in the examples that follow, zvegf4 is highly expressed in the kidney, and over-expression of zvegf4 in mice by injection of an adenovirus vector encoding zvegf4 elicits fibroproliferative changes in the kidney. Two readily identifiable features of these changes are (a) enlarged glomeruli due in part to mesangial cell proliferation, and (b) tubular regeneration due to tubule epithelial cell proliferation. These findings indicate that an increase in zvegf4 protein can modify the function of, and the interactions among, mesangial, epithelial, endothelial, smooth muscle, and interstitial cells, which are all key players in glomerular and vascular diseases of the kidney. Furthermore, zvegf4 has been found to affect cell proliferation in at least some of these cells in vitro. Experiments have also shown that the activity of zvegf4 is mediated by two PDGF receptor subunits, alpha and beta (PDGF-αR and PDGF-βR). These receptor subunits are widely expressed in most renal cell types, and their expression is upregulated in a number of kidney pathologies (e.g., Iida et al., *Proc. Natl. Acad. Sci. USA* 88:6560-6564, 1991). Stimulation of PDGF receptors has been implicated in fibroproliferative diseases of the kidney in a variety of animal models (e.g., Ooi et al., *P.S.E.B.M.* 213:230-237, 1996; Lindahl et al., *Development* 125:3313-3322, 1998; Lindahl and Betsholtz, *Curr. Op. Nephr. Hypert.* 7:21-26, 1998; and Betsholtz and Raines, *Kidney Int.* 51:1361-1369, 1997).

As also shown herein, zvegf4 has been found to stimulate the production of TGF-β by rat liver stellate cells. TGF-β is thought to be a major mediator of fibrosis, due to its ability to stimulate extracellular matrix synthesis (especially collagen and fibronectin) in a variety of mesenchymal cell types, most notably fibroblasts. TGF-β has been implicated in the development of fibrosis of the heart, lung, liver, and kidney (Ledbetter et al., *Kidney Int.* 58(6):2367-2376, 2000; Chen et al., *Mol. Cell Cardiol.* 32(10):1805-1819, 2000; Nakamura et al., *Hepatology* 32(2):247-255, 2000; Martin et al., *Int. J. Radiat. Oncol. Biol. Phys.* 47(2):277-290, 2000; Sanderson et al., *Proc. Natl. Acad. Sci. USA* 92(7):2572-2576, 1995). Increased expression of zvegf4 in organs such as the heart, kidney, lung or liver may result in fibrosis, which may at least in part be mediated and exacerbated by the enhanced production of TGF-β.

Zvegf4 has been found to be highly expressed in mouse prostate tumor cell lines as shown by Northern blotting. In addition, animals treated with a zvegf4-encoding adenovirus vector displayed invasion of the marrow space by endosteal bone, indicating an effect of zvegf4 on bone growth. In view of the high incidence of bony metastases in men suffering from prostate cancer, these results implicate zvegf4 as a mediator of prostate tumor-related cancellous bone growth.

Additional evidence indicates that zvegf4 may bind to cell-surface semaphorins, presumably via the CUB domain. Cells having cell-surface semaphorins include endothelial cells, neuronal cells, lymphocytes, and various tumor cells.

In view of the experiments summarized above and disclosed in more detail herein, it is expected that altered zvegf4 expression may initiate or exacerbate renal disease and other fibroproliferative disorders. In this context, inhibiting the action of zvegf4 using a zvegf4 antagonist will limit the progress of such disorders. Zvegf4 antagonists include, without limitation, anti-zvegf4 antibodies (including neutralizing antibodies), soluble zvegf4 receptors (including soluble PDGF beta receptor; see, e.g., Herren et al., *J. Biol. Chem.* 268:15088-15095, 1993; U.S. Pat. No. 6,018,026; and soluble PDGF alpha receptor), anti-receptor antibodies, and other peptidic and non-peptidic agents, including ribozymes, antisense polynucleotides, small molecule inhibitors, and mitogenically inactive, receptor-binding zvegf4 polypeptides.

Within the present invention zvegf4 antagonists are used to block the proliferative or profibrotic effects of zvegf4. Thus, the present invention provides methods of inhibiting, reducing, preventing, or otherwise treating fibroproliferative disorders, including, without limitation, scar formation, keloids, scleroderma, liver fibrosis, lung fibrosis, kidney fibrosis, myelofibrosis, post-surgical fibrotic adhesions, fibrotic tumors, fibroproliferative disorders of the vasculature, fibroproliferative disorders of the prostate, fibroproliferative disorders of bone, fibromatosis, fibroma, fibrosarcoma, and the like.

Fibroproliferative disorders of the kidney include, without limitation, glomerulonephritis (including membranoproliferative, diffuse proliferative, rapidly progressive, and chronic forms), diabetic glomerulosclerosis, focal glomerulosclerosis, diabetic nephropathy, lupus nephritis, tubulointerstitial fibrosis, membranous nephropathy, amyloidosis (which affects the kidney among other tissues), renal arteriosclerosis, and nephrotic syndrome. The glomerulus is a major target of many types of renal injury, including immunologic (e.g., immune-complex- or T-cell-mediated), hemodynamic (systemic or renal hypertension), metabolic (e.g., diabetes), "atherosclerotic" (accumulation of lipids in the glomerulus), infiltrative (e.g., amyloid), and toxic (e.g., snake venom) injuries (Johnson, *Kidney Mt.* 45:1769-1782, 1994). The renal structural changes in patients with diabetic nephropathy include hypertrophy of the glomerulus, thickening of the glomerular and tubular membranes (due to accumulated matrix), and increased amounts of matrix in the measangium and tubulointerstitium (Ziyadeh et al., *Proc. Natl. Acad. Sci. USA* 97:8015-8020, 2000). Glomerular hypertension due to intrarenal hemodynamic changes in diabetes can contribute to the progression of diabetic nephropathy (Ishida et al., *Diabetes* 48:595-602, 1999). Autoimmune nephritis can also lead to altered mesangial cell growth responses (Liu and Ooi, *J. Immunol.* 151:2247-2251, 1993). Infection by hepatitis-C virus can also result in idiopathic membranoproliferative glomerulonephritis (Johnson et al., *N. Engl. J. Med.* 328:465-470, 1993).

Fibroproliferative disorders of the lung include, for example, silicosis, asbestosis, idiopathic pulmonary fibrosis, bronchiolitis obliterans-organizing pneumonia, pulmonary fibrosis associated with high-dose chemotherapy, idiopathic pulmonary fibrosis, and pulmonary hypertension. These diseases are characterized by cell proliferation and increased production of extracellular matrix components, such as collagens, elastin, fibronectin, and tenascin-C.

Fibrosis of the liver can result from damage due to chronic liver disease, including chronic active hepatitis (including hepatitis C) and many other types of cirrhosis. Widespread, massive necrosis, including destruction of virtually the entire liver, can be caused by, inter alia, fulminant viral hepatitis; overdoses of the analgesic acetaminophen; exposure to other drugs and chemicals such as halothane, monoamine oxidase inhibitors, agents employed in the treatment of tuberculosis, phosphorus, carbon tetrachloride, and other industrial chemicals. Conditions associated with ultrastructural lesions that do not necessarily produce obvious liver cell necrosis include Reye's syndrome in children, tetracycline toxicity, and acute fatty liver of pregnancy. Cirrhosis, a diffuse process characterized by fibrosis and a conversion of normal architecture into structurally abnormal nodules, can come about for a variety reasons including alcohol abuse, post necrotic cirrhosis (usually due to chronic active hepatitis), biliary cirrhosis, pigment cirrhosis, cryptogenic cirrhosis, Wilson's disease, and alpha-1-antitrypsin deficiency. In cases of liver fibrosis it may be beneficial to administer a zvegf4 antagonist to suppress the activation of stellate cells, which have been implicated in the production of extracellular matrix in fibrotic liver (Li and Friedman, *J. Gastroenterol. Hepatol.* 14:618-633, 1999).

Diseases of the skeleton that are due to modified growth and matrix production in the bone include, but are not limited to, osteopetrosis, hyperostosis, osteosclerosis, osteoarthritis, and ectopic bone formation in metastatic prostate cancer. Fibroproliferative disorders of bone are characterized by aberrant and ectopic bone formation, commonly seen as active proliferation of the major cell types participating in bone formation as well as elaboration by those cells of a complex bone matrix. Exemplary of such bone disorders is the fibrosis that occurs with prostate tumor metastases to the axial skeleton. In prostate tumor-related cancellous bone growth, prostate carcinoma cells can interact reciprocally with osteoblasts to produce enhanced tumor growth and osteoblastic action when they are deposited in bone (Zhau et al., *Cancer* 88:2995-3001, 2000; Ritchie et al., *Endocrinology* 138:1145-1150, 1997). As disclosed in more detail below, mice receiving a zvegf4-encoding adenovirus vector displayed a similar pathology as that observed in prostate cancer patients who display tumor metastases in the axial skeleton and consequent formation of endosteal bone. In addition, a panel of mouse prostate cell lines (epithelial and stromal) propagated in culture were found to express very high levels of zvegf4 messenger RNA. These data suggest that zvegf4 is involved (via autocrine and/or paracrine mechanisms) in prostate tumor growth, metastasis, and effects in bone. Fibroproliferative responses of the bone originating in the skeleton per se include osteopetrosis and hyperstosis. A defect in osteoblast differentiation and function is thought to be a major cause in osteopetrosis, an inherited disorder characterized by bone sclerosis due to reduced bone resorption, wherein marrow cavities fail to develop, resulting in extramedullary hematopoiesis and severe hematologic abnormalities associated with optic atrophy, deafness, and mental retardation (Lajeunesse et al., *J. Clin Invest.* 98:1835-1842, 1996). In osteoarthritis, bone changes are known to occur, and bone collagen metabolism is increased within osteoarthritic femoral heads. The greatest changes occur within the subchondral zone, supporting a greater proportion of osteoid in the diseased tissue (Mansell and Bailey, *J. Clin. Invest.* 101:1596-1603, 1998).

Fibroproliferative disorders of the vasculature include, for example, transplant vasculopathy, which is a major cause of chronic rejection of heart transplantation. Transplant vasculopathy is characterized by accelerated atherosclerotic plaque formation with diffuse occlusion of the coronary arteries, which is a "classic" fibroproliferative disease. See, Miller et al., *Circulation* 101:1598-1605, 2000).

Antibodies used as zvegf4 antagonists include antibodies that specifically bind to a zvegf4 protein or a zvegf4 cell-surface receptor and, by so binding, reduce or prevent the binding of zvegf4 protein to the receptor and, consequently, reduce or block the receptor-mediated activity of zvegf4. As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies, and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Monoclonal antibodies can also be produced in mice that have been genetically altered to produce antibodies that have a human structure.

Methods for preparing and isolating polyclonal and monoclonal antibodies are well known in the art. See, for example, Cooligan et al. (eds.), *Current Protocols in Immunology*, National Institutes of Health, John Wiley and Sons, Inc., 1995; Sambrook et al., *Molecular Cloning: A Laboratory Manual*, second edition, Cold Spring Harbor, N.Y., 1989; and Hurrell (ed.), *Monoclonal Hybridoma Antibodies: Tech-* niques and Applications, CRC Press, Inc., Boca Raton, Fla., 1982. As would be evident to one of ordinary skill in the art, polyclonal antibodies can be generated by inoculating a variety of warm-blooded animals such as horses, cows, goats, sheep, dogs, chickens, rabbits, mice, and rats with a zvegf4 polypeptide or a fragment thereof.

Immunogenic polypeptides will comprise an epitope-bearing portion of a zvegf4 polypeptide (e.g., as shown in SEQ ID NO:2) or receptor. An "epitope" is a region of a protein to which an antibody can bind. See, for example, Geysen et al., Proc. Natl. Acad. Sci. USA 81:3998-4002, 1984. Epitopes can be linear or conformational, the latter being composed of discontinuous regions of the protein that form an epitope upon folding of the protein. Linear epitopes are generally at least 6 amino acid residues in length. Relatively short synthetic peptides that mimic part of a protein sequence are routinely capable of eliciting an antiserum that reacts with the partially mimicked protein. See, Sutcliffe et al., Science 219: 660-666, 1983. Immunogenic, epitope-bearing polypeptides contain a sequence of at least six, often at least nine, more often from 15 to about 30 contiguous amino acid residues of a zvegf4 protein or receptor. Polypeptides comprising a larger portion of a zvegf4 protein or receptor, i.e. from 30 to 50 residues up to the entire sequence are included. It is preferred that the amino acid sequence of the epitope-bearing polypeptide is selected to provide substantial solubility in aqueous solvents, that is the sequence includes relatively hydrophilic residues, and hydrophobic residues are substantially avoided (see FIGS. 1A-1G). Such regions of SEQ ID NO:2 include, for example, residues 39-44, 252-257, 102-107, 264-269, and 339-344. Exemplary longer peptide immunogens include peptides comprising residues (i) 131-148, (ii) 230-253, or (iii) 333-355 of SEQ ID NO:2. Peptide (ii) can be prepared with an additional C-terminal Cys residue and peptide (iii) with an additional N-terminal Cys residue to facilitate coupling.

The immunogenicity of a polypeptide immunogen may be increased through the use of an adjuvant, such as alum (aluminum hydroxide) or Freund's complete or incomplete adjuvant. Polypeptides useful for immunization also include fusion polypeptides, such as fusions of a zvegf4 polypeptide or a portion thereof with an immunoglobulin polypeptide or with maltose binding protein. If the polypeptide portion is "hapten-like", such portion may be advantageously joined or linked to a macromolecular carrier (such as keyhole limpet hemocyanin (KLH), bovine serum albumin (BSA), or tetanus toxoid) for immunization.

Alternative techniques for generating or selecting antibodies include in vitro exposure of lymphocytes to a polypeptide immunogen, and selection of antibody display libraries in phage or similar vectors (for instance, through use of immobilized or labeled polypeptide). Techniques for creating and screening such random peptide display libraries are known in the art (e.g., Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698), and random peptide display libraries and kits for screening such libraries are available commercially, for instance from Clontech Laboratories (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the zvegf4 sequences disclosed herein to identify proteins that bind to zvegf4.

Antibodies are determined to be specifically binding if they bind to their intended target (e.g., zvegf4 protein or receptor) with an affinity at least 10-fold greater than the binding affinity to control (e.g., non-zvegf4 or non-receptor) polypeptide or protein. In this regard, a "non-zvegf4 polypeptide" includes the related molecules VEGF, VEGF-B, VEGF-C, VEGF-D, PlGF, PDGF-A, and PDGF-B, but excludes zvegf4 polypeptides from non-human species. Due to the high level of amino acid sequence identity expected between zvegf4 orthologs, antibodies specific for human zvegf4 may also bind to zvegf4 from other species. The binding affinity of an antibody can be readily determined by one of ordinary skill in the art, for example, by Scatchard analysis (Scatchard, G., Ann. NY Acad. Sci. 51: 660-672, 1949). Methods for screening and isolating specific antibodies are well known in the art. See, for example, Paul (ed.), Fundamental Immunology, Raven Press, 1993; Getzoff et al., Adv. in Immunol. 43:1-98, 1988; Goding (ed.), Monoclonal Antibodies: Principles and Practice, Academic Press Ltd., 1996; and Benjamin et al., Ann. Rev. Immunol. 2:67-101, 1984.

A variety of assays known to those skilled in the art can be utilized to detect antibodies that specifically bind to zvegf4 proteins or receptors. Exemplary assays are described in detail in Antibodies: A Laboratory Manual, Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assays, inhibition or competition assays, and sandwich assays.

For therapeutic applications it is generally preferred to use neutralizing antibodies. As used herein, the team "neutralizing antibody" denotes an antibody that inhibits at least 50% of the biological activity of the cognate antigen when the antibody is added at a 1000-fold molar access. Those of skill in the art will recognize that greater neutralizing activity is sometimes desirable, and antibodies that provide 50% inhibition at a 100-fold or 10-fold molar access may be advantageously employed.

Zvegf4 antagonists also include soluble receptors. As used herein, a "soluble zvegf4 receptor" is a ligand-binding zvegf4 receptor polypeptide that is not bound to a cell membrane. Soluble receptors are most commonly receptor polypeptides that comprise at least a portion of the extracellular, ligand binding domain sufficient to bind ligand but lack transmembrane and cytoplasmic domains. Many cell-surface receptors have naturally occurring, soluble counterparts that are produced by proteolysis. Receptor polypeptides are said to be substantially free of transmembrane and intracellular polypeptide segments when they lack sufficient portions of these segments to provide membrane anchoring or signal transduction, respectively. Soluble receptors can comprise additional amino acid residues, such as affinity tags that provide for purification of the polypeptide or provide sites for attachment of the polypeptide to a substrate, or immunoglobulin constant region sequences. Dimeric and higher order multimeric soluble receptors are preferred for their ability to bind ligand with high affinity. A soluble receptor can be prepared as a fusion to a dimerizing protein as disclosed in U.S. Pat. Nos. 5,155,027 and 5,567,584. Dimerizing proteins in this regard include, for example, immunoglobulin fragments comprising constant region and hinge domains (e.g., IgG Fc fragments).

Zvegf4 antagonists further include antisense polynucleotides, which can be used to inhibit zvegf4 gene transcription and thereby inhibit cell activation and/or proliferation in vivo. Polynucleotides that are complementary to a segment of a zvegf4-encoding polynucleotide (e.g., a polynucleotide as set forth in SEQ ID NO:1) are designed to bind to zvegf4-encoding mRNA and to inhibit translation of such mRNA. Antisense polynucleotides can be targeted to specific tissues using a gene therapy approach with specific vectors and/or promoters, such as viral delivery systems as disclosed in more detail below.

Ribozymes can also be used as zvegf4 antagonists within the present invention. Ribozymes are RNA molecules that contains a catalytic center and a target RNA binding portion. The term includes RNA enzymes, self-splicing RNAs, self-cleaving RNAs, and nucleic acid molecules that perform these catalytic functions. A ribozyme selectively binds to a target RNA molecule through complementary base pairing, bringing the catalytic center into close proximity with the target sequence. The ribozyme then cleaves the target RNA and is released, after which it is able to bind and cleave additional molecules. A nucleic acid molecule that encodes a ribozyme is termed a "ribozyme gene." Ribozymes can be designed to express endonuclease activity that is directed to a certain target sequence in a mRNA molecule (see, for example, Draper and Macejak, U.S. Pat. No. 5,496,698, McSwiggen, U.S. Pat. No. 5,525,468, Chowrira and McSwiggen, U.S. Pat. No. 5,631,359, and Robertson and Goldberg, U.S. Pat. No. 5,225,337). An expression vector can be constructed in which a regulatory element is operably linked to a nucleotide sequence that encodes a ribozyme.

In another approach, expression vectors can be constructed in which a regulatory element directs the production of RNA transcripts capable of promoting RNase P-mediated cleavage of mRNA molecules that encode a zvegf4 polypeptide. According to this approach, an external guide sequence can be constructed for directing the endogenous ribozyme, RNase P, to a particular species of intracellular mRNA, which is subsequently cleaved by the cellular ribozyme (see, for example, Altman et al., U.S. Pat. No. 5,168,053; Yuan et al., *Science* 263:1269, 1994; Pace et al., WIPO Publication No. WO 96/18733; George et al., WIPO Publication No. WO 96/21731; and Werner et al., WIPO Publication No. WO 97/33991). An external guide sequence generally comprises a ten- to fifteen-nucleotide sequence complementary to zvegf4 mRNA, and a 3'-NCCA nucleotide sequence, wherein N is preferably a purine. The external guide sequence transcripts bind to the targeted mRNA species by the formation of base pairs between the mRNA and the complementary external guide sequences, thus promoting cleavage of mRNA by RNase P at the nucleotide located at the 5'-side of the base-paired region.

The growth factor domain of zvegf4 has been found to be an active species of the molecule that binds to cell-surface PDGF receptors competitively with other PDGF isoforms. Proteolytic processing to remove the N-terminal portion of the molecule is required for this activity. Thus, inhibitors of this proteolytic activation can also be used as zvegf4 antagonists within the present invention.

For pharmaceutical use, zvegf4 antagonists are formulated for topical or parenteral, particularly intravenous or subcutaneous, delivery according to conventional methods. In general, pharmaceutical formulations will include a zvegf4 antagonist in combination with a pharmaceutically acceptable vehicle, such as saline, buffered saline, 5% dextrose in water, or the like. Formulations may further include one or more excipients, preservatives, solubilizers, buffering agents, albumin to prevent protein loss on vial surfaces, etc. Methods of formulation are well known in the art and are disclosed, for example, in *Remington: The Science and Practice of Pharmacy*, Gennaro, ed., Mack Publishing Co., Easton, Pa., 19th ed., 1995. A "therapeutically effective amount" of a composition is that amount that produces a statistically significant effect, such as a statistically significant reduction in disease progression or a statistically significant improvement in organ function. The exact dose will be determined by the clinician according to accepted standards, taking into account the nature and severity of the condition to be treated, patient traits, etc. Determination of dose is within the level of ordinary skill in the art. The therapeutic formulations will generally be administered over the period required to achieve a beneficial effect, commonly up to several months and, in treatment of chronic conditions, for a year or more. Dosing is daily or intermittently over the period of treatment. Intravenous administration will be by bolus injection or infusion over a typical period of one to several hours. Sustained release formulations can also be employed. For treatment of pulmonary fibrosis, a zvegf4 antagonist can be delivered by aerosolization according to methods known in the art. See, for example, Wang et al., U.S. Pat. No. 5,011,678; Gonda et al., U.S. Pat. No. 5,743,250; and Lloyd et al., U.S. Pat. No. 5,960,792.

Other mitogenic factors, including the PDGFs, EGF, TGF-$\beta$1 and TGF-$\beta$2, and FGFs, have been implicated in the initiation or perpetuation of fibrosis. It may therefore be advantageous to combine a zvegf4 antagonist with one or more antagonists of these other factors.

Antibodies are preferably administered parenterally, such as by bolus injection or infusion (intravenous, intramuscular, intraperitoneal, or subcutaneous) over the course of treatment. Antibodies are generally administered in an amount sufficient to provide a minimum circulating level of antibody throughout the treatment period of between approximately 20 $\mu$g and 1 mg/kg body weight. In this regard, it is preferred to use antibodies having a circulating half-life of at least 12 hours, preferably at least 4 days, more preferably up to 14-21 days. Chimeric and humanized antibodies are expected to have circulatory half-lives of up to four and up to 14-21 days, respectively. In many cases it will be preferable to administer daily doses during a hospital stay, followed by less frequent bolus injections during a period of outpatient treatment. Antibodies can also be delivered by slow-release delivery systems, pumps, and other known delivery systems for continuous infusion. Dosing regimens may be varied to provide the desired circulating levels of a particular antibody based on its pharmacokinetics. Thus, doses will be calculated so that the desired circulating level of therapeutic agent is maintained. Daily doses referred to above may be administered as larger, less frequent bolus administrations to provide the recited dose averaged over the term of administration.

Those skilled in the art will recognize that the same principles will guide the use of other zvegf4 antagonists. The dosing regimen for a given antagonist will be determined by a number of factors including potency, pharmacokinetics, and the physicochemical nature of the antagonist. For example, non-peptidic zvegf4 antagonists may be administered enterally.

Therapeutic polynucleotides, such as antisense polynucleotides, can be delivered to patients or test animals by way of viral delivery systems. Exemplary viruses for this purpose include adenovirus, herpesvirus, retroviruses, vaccinia virus, and adeno-associated virus (AAV). Adenovirus, a double-stranded DNA virus, is currently the best studied gene transfer vector for delivery of heterologous nucleic acids. For review, see Becker et al., *Meth. Cell Biol.* 43:161-189, 1994; and Douglas and Curiel, *Science & Medicine* 4:44-53, 1997. The adenovirus system offers several advantages. Adenovirus can (i) accommodate relatively large DNA inserts; (ii) be grown to high-titer; (iii) infect a broad range of mammalian cell types; and (iv) be used with many different promoters, including ubiquitous, tissue specific, and regulatable promoters. Because adenoviruses are stable in the bloodstream, they can be administered by intravenous injection.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. When intravenously administered to intact animals, adenovirus primarily targets the liver. If the adenoviral delivery system has an E1 gene deletion, the virus cannot replicate in the host cells. However, the host's tissue (e.g., liver) will express and process (and, if a signal sequence is present, secrete) the heterologous protein.

An alternative method of gene delivery comprises removing cells from the body and introducing a vector into the cells as a naked DNA plasmid. The transformed cells are then re-implanted in the body. Naked DNA vectors are introduced into host cells by methods known in the art, including transfection, electroporation, microinjection, transduction, cell fusion, DEAE dextran, calcium phosphate precipitation, use of a gene gun, or use of a DNA vector transporter. See, Wu et al., *J. Biol. Chem.* 263:14621-14624, 1988; Wu et al., *J. Biol. Chem.* 267:963-967, 1992; and Johnston and Tang, *Meth. Cell Biol.* 43:353-365, 1994.

Zvegf4 antagonists can be analyzed for receptor-binding activity or inhibition of zvegf4-receptor binding by a variety of methods that are well known in the art, including receptor competition assays (Bowen-Pope and Ross, *Methods Enzymol.* 109:69-100, 1985) and through the use of soluble receptors, including receptors produced as IgG fusion proteins (U.S. Pat. No. 5,750,375). Receptor-binding assays can be performed on cell lines that contain cell-surface receptors for zvegf4. The receptors can be naturally present in the cell, or can be recombinant receptors expressed by genetically engineered cells.

Activity of zvegf4 antagonists can be measured in vitro using cultured cells in assays designed to measure zvegf4 activity. Antagonists will reduce the effects of zvegf4 within the assay. Mitogenic activity can be measured using known assays, including $^3$H-thymidine incorporation assays (as disclosed by, e.g., Raines and Ross, *Methods Enzymol.* 109:749-773, 1985 and Wahl et al., *Mol. Cell Biol.* 8:5016-5025, 1988), dye incorporation assays (as disclosed by, for example, Mosman, *J. Immunol. Meth.* 65:55-63, 1983 and Raz et al., *Acta Trop.* 68:139-147, 1997) or cell counts. Exemplary mitogenesis assays measure incorporation of $^3$H-thymidine into (1) 20% confluent cultures to look for the ability of zvegf4 proteins to further stimulate proliferating cells, and (2) quiescent cells held at confluence for 48 hours to look for the ability of zvegf4 proteins to overcome contact-induced growth inhibition. Exemplary dye incorporation assays include measurement of the incorporation of the dye Alamar blue (Raz et al., ibid.) into target cells. See also, Gospodarowicz et al., *J. Cell. Biol.* 70:395-405, 1976; Ewton and Florini, *Endocrinol.* 106:577-583, 1980; and Gospodarowicz et al., *Proc. Natl. Acad. Sci. USA* 86:7311-7315, 1989.

The biological activities of zvegf4 antagonists can be studied in non-human animals by administration of exogenous compounds, by expression of zvegf4 inhibitory polynucleotides, and by suppression of endogenous zvegf4 expression through knock-out techniques. Viral delivery systems (disclosed above) can be employed. Zvegf4 antagonists can be administered or expressed individually, in combination with other zvegf4 antagonists, or in combination other compounds, including other growth factor antagonists. Test animals are monitored for changes in such parameters as clinical signs, body weight, blood cell counts, clinical chemistry, histopathology, and the like.

Effects of zvegf4 antagonists on liver and kidney fibrosis can be tested in known animal models, such as the db/db mouse model disclosed by Cohen et al., *Diabetologia* 39:270-274, 1996 and Cohen et al., *J. Clin. Invest.* 95:2338-2345, 1995, or transgenic animal models (Imai et al., *Contrib. Nephrol.* 107:205-215, 1994).

Effects on lung fibrosis can also be assayed in a mouse model using bleomycin. The chemotherapy agent bleomycin is a known causative agent of pulmonary fibrosis in humans and can induce interstitial lung disease in mice, including an increase in the number of fibroblasts, enhanced collagen deposition, and dysregulated matrix remodeling. C57Bl/6 mice are administered bleomycin by osmotic minipump for 1 week. There follows a period of inflammation, with cutaneous toxicity beginning approximately 4-7 days after bleomycin administration and continuing for about a week, after which the mice appear to regain health. About 3-4 weeks after the finish of bleomycin delivery, the mice are sacrificed, and the lungs are examined histologically for signs of fibrosis. Scoring is based on the extent of lung fibrotic lesions and their severity. Serum is assayed for lactic dehydrogenase, an intracellular enzyme that is released into the circulation upon general cell death or injury. Lung tissue is assayed for hydroxyproline as a measure of collagen deposition.

Mice and other animals carrying a zvegf4-expressing adenovirus vector are also useful models for testing zvegf4 antagonists and other antifibroproliferative agents.

The invention is further illustrated by the following, non-limiting examples.

EXAMPLES

Example 1

Zvegf4 was identified from the sequence of a clone from a human chronic myelogenous leukemia cell (K562) library by its homology to the VEGF family. Additional sequence was elucidated from a long sequence read of a clone from a pituitary library. An antisense expressed sequence tag (EST) for zvegf4 was found, for which its 5' partner was identified. This 5' EST (EST448186; GenBank) appeared to contain the 5' untranslated sequence for zvegf4. A primer was designed from EST448186 to close the gap in the sequence. 20 pm each of oligonucleotides ZC21,987 (SEQ ID NO:5) and ZC21,120 (SEQ ID NO:6), and 1.93 µg of a thyroid library were used in the PCR reaction with 5% DMSO and 1/10 volume of a commercial reagent (GC-MELT; Clontech Laboratories, Inc., Palo Alto, Calif.). The reaction was run for 1 minute at 94 degrees; then 30 cycles of 94 degrees, 20 seconds; 67 degrees, 1 minute; then a final 5-minute incubation at 72 degrees. A resulting 833-bp product was sequenced and found to be a zvegf4 fragment containing the remainder of the coding sequence with an initiation MET codon, upstream stop codon, and 5' untranslated sequence. The composite sequence included an open reading frame of 1,110 bp (SEQ ID NO:1).

Example 2

A partial mouse zvegf4 sequence was obtained by probing a mouse genomic library (obtained from Clontech Laboratories, Inc.) with a 1,289 bp EcoRI human zvegf4 restriction digest fragment containing the entire coding sequence. The probe was labeled with $^{32}$P using a commercially available kit (REDIPRIME II random-prime labeling system; Amersham Pharmacia, Buckinghamshire, England). Unincorporated radioactivity was removed using a commercially available push column (NUCTRAP column; Stratagene, La Jolla, Calif.; see U.S. Pat. No. 5,336,412). Twenty-four filter lifts were prehybridized overnight at 50° C. in a hybridization solution (EXPRESSHYB Hybridization Solution; Clontech Laboratories, Inc.) containing 0.1 mg/ml salmon sperm DNA that had been boiled 5 minutes, then iced. Filters were hybridized overnight at 50° C. in hybridization solution (EXPRESSHYB) containing $1.0 \times 10^6$ cpm/ml zvegf4 probe, 0.1 mg/ml salmon sperm DNA, and 0.5 µg/ml mouse cot-1 DNA that had been boiled 5 minutes, then iced. Filter lifts were washed in 2×SSC, 0.1% SDS at room temperature for 2 hours, then the temperature was raised to 60° C. for one hour. Overnight exposure at −80° C. showed 7 putative primary hits.

Four of the primary hits were plated on a lawn of *E. coli* K802 cells (obtained from Clontech Laboratories, Inc.). Filter lifts were prepared and hybridized overnight with the human zvegf4 probe. Two of the 4 primary putative hits that were tested came up positive.

DNA was prepared from one positive plaque and digested with BamHI and PstI. The digest was run on a 1% Tris-Borate-EDTA gel, and a 2.0 kb doublet and 2.7 kb/2.9 kb bands were excised from the gel and extracted from the agarose by conventional methods. Both 2.0 kb fragments were found to strongly hybridize to the human zvegf4 probe. These fragments were sequenced and found to contain part of the mouse zvegf4 CUB domain. Primers were designed from the sequence for use in a PCR cDNA screen.

A panel of mouse cDNAs was screened by PCR with primers ZC26,317 (SEQ ID NO:7) and ZC26,318 (SEQ ID NO:8). Embryo, salivary gland, neonatal skin, and testis showed strong products of the predicted 200 bp size.

Mouse testis and salivary gland libraries were screened by PCR using primers ZC26,317 (SEQ ID NO:7) and ZC26,318 (SEQ ID NO:8). The testis library yielded one clone, named "zvegf4mpzp7x-6", that was incomplete at the 5' end and appeared to contain an intron at the 5' end. The salivary gland library yielded one clone, named "zvegf4mpzp7x-7", that had a 225-bp deletion in coding compared to clone zvegf4mpzp7x-6. The sequences derived from zvegf4mpzp7x-6 and zvegf4mpzp7x-7 were combined to produce a full-length mouse zvegf4 polynucleotide sequence (SEQ ID NO:3) and mouse zvegf4 polypeptide sequence (SEQ ID NO:4).

A full-length cDNA clone was generated by a two-step ligation of fragments from the two clones. An EcoRI/HindIII 3' fragment was prepared from clone zvegf4mpzp7x-6. The 528-bp fragment was gel-purified and ligated into a phagemid vector (PBLUESCRIPT II KS(+); Stratagene) that had been digested with EcoRI and HindIII. Three µg of the resulting construct was digested with 15 units of EcoRI. The linearized plasmid was purified and ligated with a 754-bp 5' EcoRI fragment from clone zvegf4mpzp7x-7.

Example 3

Recombinant human zvegf4 having a carboxyl-terminal Glu-Glu affinity tag was produced in a baculovirus expression system according to conventional methods. The culture was harvested, and the cells were lysed with a solution of 0.02 M Tris-HCl, pH 8.3, 1 mM EDTA, 1 mM DTT, 1 mM 4-(2-Aminoethyl)-benzenesulfonyl fluoride hydrochloride (PEFABLOC SC; Boehringer-Mannheim), 0.5 µM aprotinin, 4 mM leupeptin, 4 mM E-64, 1% NP-40 at 4° C. for 15 minutes on a rotator. The solution was centrifuged, and the supernatant was recovered. Twenty ml of extract was combined with 50 µl of anti-Glu-Glu antibody conjugated to derivatized agarose beads (SEPHAROSE; Amersham Pharmacia Biotech Inc., Piscataway, N.J.) in 50 µl buffer. The mixture was incubated on a rotator at 4° C. overnight. The beads were recovered by centrifugation and washed 3×15 minutes at 4° C. Pellets were combined with sample buffer containing reducing agent and heated at 98° C. for five minutes. The protein was analyzed by polyacrylamide gel electrophoresis under reducing conditions followed by western blotting on a PVDF membrane using an antibody to the affinity tag. Two bands were detected, one a $M_r \approx 49$ kD and the other at $M_r \approx 21$ kD. Sequence analysis showed the larger band to comprise two sequences, one beginning at Arg-19 of SEQ ID NO:2 and the other beginning at Asn-35 of SEQ ID NO:2. The asparagine residue appeared to have been deamidated to an aspartic acid. The smaller band began at Ser-250 of SEQ ID NO:2.

Example 4

To prepare adenovirus vectors, the protein coding region of zvegf4 is amplified by PCR using primers that add FseI and AscI restriction sites at the 5' and 3' termini, respectively. PCR primers are used with a template containing the full-length zvegf4 cDNA in a PCR reaction as follows: incubation at 95° C. for 5 minutes; followed by 15 cycles at 95° C. for 1 min., 58° C. for 1 min., and 72° C. for 1.5 min.; followed by 72° C. for 7 min.; followed by a 4° C. soak. The reaction products are loaded onto a 1.2% low-melt agarose (SEAPLAQUE GTG™; FMC, Rockland, Me.) gel in TAE buffer. The zvegf4 PCR product is excised from the gel and purified using a spin column containing a silica gel membrane (QIAQUICK Gel Extraction Kit; Qiagen, Inc., Valencia, Calif.) as per kit instructions. The zvegf4 product is then digested, phenol/chloroform extracted, EtOH precipitated, and rehydrated in 20 ml TE (Tris/EDTA pH 8). The zvegf4 fragment is then ligated into the cloning sites of the transgenic vector pTG12-8. Vector pTG12-8 was derived from p2999B4 (Palmiter et al., *Mol. Cell Biol.* 13:5266-5275, 1993) by insertion of a rat insulin II intron (ca. 200 bp) and polylinker (Fse I/Pme I/Asc I) into the Nru I site. The vector comprises a mouse metallothionein (MT-1) promoter (ca. 750 bp) and human growth hormone (hGH) untranslated region and polyadenylation signal (ca. 650 bp) flanked by 10 kb of MT-1 5' flanking sequence and 7 kb of MT-1 3' flanking sequence. The construct is transformed into *E. coli* host cells (ELECTROMAX DH10B™ cells; obtained from Life Technologies, Inc., Gaithersburg, Md.) by electroporation. Clones containing zvegf4 DNA are identified by restriction analysis. A positive clone is confirmed by direct sequencing.

The zvegf4 cDNA is released from the pTG12-8 vector using FseI and AscI enzymes. The cDNA is isolated on a 1% low melt agarose gel, and is then excised from the gel. The gel slice is melted at 70° C., extracted twice with an equal volume of Tris-buffered phenol, and EtOH precipitated. The DNA is resuspended in 10 µl $H_2O$.

The zvegf4 cDNA is cloned into the FseI-AscI sites of a modified pAdTrack CMV (He et al., *Proc. Natl. Acad. Sci. USA* 95:2509-2514, 1998). This construct contains a green fluorescent protein (GFP) marker gene. The CMV promoter driving GFP expression has been replaced with the SV40 promoter, and the SV40 polyadenylation signal has been replaced with the human growth hormone polyadenylation signal. In addition, the native polylinker has been replaced with FseI, EcoRV, and AscI sites. This modified form of pAdTrack CMV is named pZyTrack. Ligation is performed using a DNA ligation and screening kit (FAST-LINK; Epicentre Technologies, Madison, Wis.). In order to linearize the plasmid, approximately 5 µg of the pZyTrack zvegf4 plasmid is digested with PmeI. Approximately 1 µg of the linearized plasmid is cotransformed with 200 ng of supercoiled pAdEasy (He et al., ibid.) into BJ5183 cells. The co-transformation is done using a Bio-Rad Gene Pulser at 2.5 kV, 200 ohms and 25 µF. The entire co-transformation is plated on 4 LB plates containing 25 µg/ml kanamycin. The smallest colonies are picked and expanded in LB/kanamycin, and recombinant adenovirus DNA is identified by standard DNA miniprep procedures. Digestion of the recombinant adenovirus DNA with FseI and AscI confirms the presence of zvegf4 DNA. The recombinant adenovirus miniprep DNA is transformed into E. coli DH10B competent cells, and DNA is prepared therefrom.

Approximately 5 µg of recombinant adenoviral DNA is digested with Pad enzyme (New England Biolabs) for 3 hours at 37° C. in a reaction volume of 100 µl containing 20-30 U of PacI. The digested DNA is extracted twice with an equal volume of phenol/chloroform and precipitated with ethanol. The DNA pellet is resuspended in 10 µl distilled water. A T25 flask of QBI-293A cells (Quantum Biotechnologies, Inc., Montreal, Canada), inoculated the day before and grown to 60-70% confluence, are transfected with the Pad digested DNA. The PacI-digested DNA is diluted up to a total volume of 50 µl with sterile HBS (150 mM NaCl, 20 mM HEPES). In a separate tube, 20 µl of 1 mg/ml N-[1-(2,3-Dioleoyloxy) propyl]-N,N,N-trimethyl-ammonium methylsulfate (DOTAP; Boehringer Mannheim) is diluted to a total volume of 100 µl with HBS. The DNA is added to the DOTAP, mixed gently by pipeting up and down, and left at room temperature for 15 minutes. The media is removed from the 293A cells and washed with 5 ml serum-free MEM-alpha (Life Technologies, Gaithersburg, Md.) containing 1 mM sodium pyruvate (Life Technologies), 0.1 mM MEM non-essential amino acids (Life Technologies) and 25 mM HEPES buffer (Life Technologies). 5 ml of serum-free MEM is added, and the cells are held at 37° C. The DNA/lipid mixture is added drop-wise to the flask, mixed gently, and incubated at 37° C. for 4 hours. After 4 hours the media containing the DNA/lipid mixture is aspirated off and replaced with 5 ml complete MEM containing 5% fetal bovine serum. The transfected cells are monitored for GFP expression and formation of foci (viral plaques).

Seven days after transfection of 293A cells with the recombinant adenoviral DNA, cells expressing GFP start to form foci. The crude viral lysate is harvested by using a cell scraper to collect the cells. The lysate is transferred to a 50 ml conical tube. To release most of the virus particles from the cells, three freeze/thaw cycles are done in a dry ice/ethanol bath and a 37° C. waterbath.

Ten 10-cm plates of nearly confluent (80-90%) 293A cells are set up 20 hours prior to infection. The crude lysate is amplified (primary amplification) to obtain a working stock of zvegf4 recombinant adenovirus (rAdV) lysate. 200 ml of crude rAdV lysate is added to each 10-cm plate, and the plates are monitored for 48 to 72 hours looking for cytopathic effect (CPE) under the white light microscope and expression of GFP under the fluorescent microscope. When all of the cells show CPE, this 1° stock lysate is collected, and freeze/thaw cycles are performed as described above.

Secondary (2°) amplification of zvegf4 rAdV is obtained from twenty 15-cm tissue culture dishes of 80-90% confluent 293A cells. All but 20 ml of 5% MEM media is removed, and each dish is inoculated with 300-500 ml of 1° amplified rAdv lysate. After 48 hours the cells are lysed from virus production, the lysate is collected into 250 ml polypropylene centrifuge bottles, and the rAdV is purified.

NP-40 detergent is added to a final concentration of 0.5% to the bottles of crude lysate to lyse all cells. Bottles are placed on a rotating platform for 10 minutes and agitated as fast as possible. The debris is pelleted by centrifugation at 20,000×G for 15 minutes. The supernatant is transferred to 250-ml polycarbonate centrifuge bottles, and 0.5 volume of 20% PEG8000/2.5M NaCl solution is added. The bottles are shaken overnight on ice. The bottles are centrifuged at 20,000×G for 15 minutes, and the supernatants are discarded into a bleach solution. A white precipitate (precipitated virus/PEG) forms in two vertical lines along the walls of the bottles on either side of the spin mark. Using a sterile cell scraper, the precipitate from 2 bottles is resuspended in 2.5 ml PBS. The virus solution is placed in 2-ml microcentrifuge tubes and centrifuged at 14,000×G in a microcentrifuge for 10 minutes to remove any additional cell debris. The supernatants from the 2-ml microcentrifuge tubes are transferred into a 15-ml polypropylene snapcap tube and adjusted to a density of 1.34 g/ml with CsCl. The volume of the virus solution is estimated, and 0.55 g/ml of CsCl is added. The CsCl is dissolved, and 1 ml of this solution is weighed. The solution is transferred to polycarbonate, thick-walled, 3.2 ml centrifuge tubes (Beckman) and spun at 348,000 X G for 3-4 hours at 25° C. The virus forms a white band. Using wide-bore pipette tips, the virus band is collected.

The virus recovered from the gradient includes a large amount of CsCl, which must be removed before it can be used on cells. Pharmacia PD-10 columns prepacked with SEPHADEX G-25M (Pharmacia) are used to desalt the virus preparation. The column is equilibrated with 20 ml of PBS. The virus is loaded and allowed to run into the column. 5 ml of PBS is added to the column, and fractions of 8-10 drops collected. The optical density of a 1:50 dilution of each fraction is determined at 260 nm on a spectrophotometer, and a clear absorbance peak is identified. Peak fractions are pooled, and the optical density (OD) of a 1:25 dilution is determined. OD is converted into virus concentration using the formula (OD at 260 nm)(25)($1.1 \times 10^{12}$)=virions/ml.

To store the virus, glycerol is added to the purified virus to a final concentration of 15%, mixed gently and stored in aliquots at −80° C.

A protocol developed by Quantum Biotechnologies, Inc. (Montreal, Canada) is followed to measure recombinant virus infectivity. Briefly, two 96-well tissue culture plates are seeded with $1 \times 10^4$ 293A cells per well in MEM containing 2% fetal bovine serum for each recombinant virus to be assayed. After 24 hours, 10-fold dilutions of each virus from $1 \times 10^{-2}$ to $1 \times 10^{-14}$ are made in MEM containing 2% fetal bovine serum. 100 µl of each dilution is placed in each of 20 wells. After 5 days at 37° C., wells are read either positive or negative for CPE, and PFU/ml is calculated.

$TCID_{50}$ formulation used is as per Quantum Biotechnologies, Inc., above. The titer (T) is determined from a plate where virus used is diluted from $10^{-2}$ to $10^{-14}$, and read 5 days after the infection. At each dilution a ratio (R) of positive wells for CPE per the total number of wells is determined. The titer of the undiluted sample is $T=10^{(1+F)}=TCID_{50}/ml$, where $F=1+d(S-0.5)$, S is the sum of the ratios (R), and d is $Log_{10}$ of the dilution series (e.g., d=1 for a ten-fold dilution series). To convert $TCID_{50}/ml$ to pfu/ml, 0.7 is subtracted from the exponent in the calculation for titer (T).

Example 5

The human zvegf4 cDNA was cloned into the EcoRV-AscI sites of pZyTrack (Example 4). Ligation was performed using a commercially available DNA ligation and screening kit (FAST-LINK kit; Epicentre Technologies, Madison, Wis.).

Zvegf4 was assayed in an aortic ring outgrowth assay (Nicosia and Ottinetti, *Laboratory Investigation* 63:115, 1990; Villaschi and Nicosia, *Am. J. Pathology* 143:181-190, 1993). Thoracic aortas were isolated from 1-2 month old Sprague-Dawley male rats and transferred to petri dishes containing HANK's buffered salt solution. The aortas were flushed with additional HANK's buffered salt solution to remove blood, and adventitial tissue surrounding the aortas was carefully removed. Cleaned aortas were transferred to petri dishes containing EBM basal media, serum free (Clonetics, San Diego, Calif.). Aortic rings were obtained by slicing approximately 1-mm sections using a scalpel blade. The ends of the aortas used to hold them in place were not used. The rings were rinsed in fresh EBM basal media and placed individually in wells of a 24-well plate coated with basement membrane matrix (MATRIGEL; Becton Dickinson, Franklin Lakes, N.J.). The rings were overlayed with an additional 50 μl of the matrix solution and placed at 37° C. for 30 minutes to allow the matrix to gel. Test samples were diluted in EBM basal serum-free media supplemented with 100 units/ml penicillin, 100 μg/ml streptomycin and HEPES buffer and added at 1 ml/well. Background control was EBM basal serum-free media alone. Basic FGF (R&D Systems, Minneapolis, Minn.) at 20 ng/ml was used as a positive control. Zvegf4 adenovirus was added to wells, assuming a cell count of 500,000 cells and a multiplicity of infection of 5000 particles/cell. A null adenovirus (designated "zPar") was used as a control. Samples were added in a minimum of quadruplets. Rings were incubated for 5-7 days at 37° C. and analyzed for growth. Aortic outgrowth was scored by multiple, blinded observers using 0 as no growth and 4 as maximum growth. Zvegf4 adenovirus produced a significant increase in outgrowth, comparable to the bFGF control.

Zvegf4 adenovirus infection produced a significant increase in the outgrowth of cells as compared to parental virus control. Cells isolated from the matrix surrounding the aortic ring were identified as fibroblasts or smooth muscle cells (SMC) by staining for alpha smooth muscle actin (characteristic of SMCs), and vimentin and type I collagen (characteristic of fibroblasts). In contrast, there were no endothelial cells detected as indicated by the absence of staining for von Willebrand's factor, a specific endothelial marker.

Potent induction of cellular outgrowth, similar to that induced by purified PDGF-AA and PDGF-BB, was also observed following treatment with purified growth factor domain (mature) zvegf4. These patterns of outgrowth were unlike that seen following VEGF treatment, which produced sparser endothelial sprouts. The ability of zvegf4 to induce a response similar to that of PDGF-AA and PDGF-BB, that is a smooth muscle and fibroblast migratory and cyto-kinetic response, correlated with the involvement of PDGF receptor stimulation in fibroproliferative responses of the vasculature.

Example 6

Polyclonal anti-peptide antibodies were prepared by immunizing 2 female New Zealand white rabbits with the peptides huzvegf4-1 (SEQ ID NO:9), huzvegf4-2 (SEQ ID NO:10), or huzvegf4-3 (SEQ ID NO:11). The peptides were synthesized using an Applied Biosystems Model 431A peptide synthesizer (Applied Biosystems, Inc., Foster City, Calif.) according to the manufacturer's instructions. The peptides were conjugated to keyhole limpet hemocyanin (KLH) with maleimide activation. The rabbits were each given an initial intraperitoneal (ip) injection of 200 μg of peptide in Complete Freund's Adjuvant followed by booster ip injections of 100 μg peptide in Incomplete Freund's Adjuvant every three weeks. Seven to ten days after the administration of the second booster injection (3 total injections), the animals were bled, and the sera were collected. The animals were then boosted and bled every three weeks.

The zvegf4 peptide-specific rabbit sera were characterized by an ELISA titer check using 1 μg/ml of the peptide used to make the antibody as an antibody target. The 2 rabbit sera to the huzvegf4-1 peptide had titer to their specific peptide at a dilution of 1:5,000,000. The 2 rabbit sera to the huzvegf4-2 peptide had titer to their specific peptide at a dilution of 1:5,000,000. The 2 rabbit sera to the huzvegf4-3 peptide had titer to their specific peptide at a dilution of 1:500,000.

The zvegf4 peptide-specific polyclonal antibodies were affinity purified from the sera using CNBr-SEPHAROSE 4B protein columns (Pharmacia LKB) that were prepared using 10 mg of the specific peptide per gram CNBr-SEPHAROSE, followed by 20× dialysis in PBS overnight. Zvegf4-specific antibodies were characterized by an ELISA titer check using 1 μg/ml of the appropriate peptide antigens as antibody targets. The lower limit of detection (LLD) of the anti-huzvegf4-1 affinity purified antibody on its specific antigen (huzvegf4-1 peptide) was a dilution of 0.1 pg/ml. The LLD of the anti-huzvegf4-2 affinity purified antibody on its specific antigen (huzveg4-2 peptide) was a dilution of 5 ng/ml. The LLD of the rabbit anti-huzvegf4-3 affinity purified antibody on its specific antigen (huzvegf4-3 peptide) was a dilution of 5 ng/ml.

Example 7

Recombinant amino-terminally Glu-Glu-tagged zvegf4 growth factor domain with an amino-tell final Glu-Glu (EYMPME; SEQ ID NO:12) tag (zvegf4-nee-GFD) was produced from recombinant baculovirus-infected insect cells. 28-liter cultures were harvested, and the media were filtered using a 0.45 μm filter. Protein was purified from the conditioned media by a combination of cation-exchange chromatography, antibody affinity chromatography, and size-exclusion chromatography. Cultured medium (pH 7.0, conductivity 9 mS) was directly loaded onto a 25-ml cation exchange column (POROS 50 HS; PerSeptive Biosystems, Framingham, Mass.). The column was washed with ten column volumes (cv) of PBS, and the bound protein was eluted with a gradient of 20-100% of 750 mM NaCl in PBS (Buffer B) for 15 cv followed by 5 cv of 100% Buffer B at 5 Five-ml fractions were collected. Samples from the column were analyzed by SDS-PAGE with silver staining and western blotting for the presence of zvegf4-nee-GFD. Zvefg4-nee-GFD-containing fractions were pooled and loaded onto an 8-ml anti-Glu-Glu antibody column and eluted with 50 ml of 0.5 mg/ml EYMPTD (SEQ ID NO:13) peptide (obtained from Princeton Biomolecules Corporation, Langhorne, Pa.) in PBS. One-ml fractions were pooled and concentrated to 4 ml using a BIOMAX-5 concentrator (Millipore Corp., Bedford, Mass.) and loaded onto a 16×1000 mm gel filtration column (SEPHACRYL S-100 HR; Amersham Pharmacia Biotech, Piscataway, N.J.) at 1.5 ml/minute. Five-ml fractions containing purified zvegf4-nee-GFD were pooled, filtered through a 0.2 μm filter, aliquoted into 100 μl aliquots, and frozen at −80° C. The concentration of the final purified protein was determined by BCA assay (Pierce Chemical Co., Rockford, Ill.) to be 0.4 mg/ml, and the yield was calculated to be 8.4 mg.

Recombinant zvegf4-nee-GFD was analyzed by SDS-PAGE (NUPAGE 4-12% gel; Novex, San Diego, Calif.) with silver staining (FASTSILVER, Geno Technology, Inc., Maplewood, Mo.) and Western blotting using antibodies to the peptide tag. Conditioned media or purified protein was electrophoresed using an electrophoresis mini-cell (XCELL II mini-cell; Novex) and transferred to nitrocellulose (0.2 µm; Novex) at room temperature using a blot module (XCELL II; Novex) with stirring according to directions provided in the instrument manual. The transfer was run at 500 mA for one hour in a buffer containing 25 mM Tris base, 200 mM glycine, and 20% methanol. The filters were then blocked with 10% non-fat dry milk in PBS for 10 minutes at room temperature. The nitrocellulose was quickly rinsed, then the mouse anti-peptide primary antibody was added, diluted 1:1000 in PBS containing 2.5% non-fat dry milk. The blots were incubated for two hours at room temperature or overnight at 4° C. with gentle shaking. Following the incubation, blots were washed three times for 10 minutes each in PBS, then labeled with a secondary antibody (goat anti-mouse IgG conjugated to horseradish peroxidase) diluted 1:1000 in PBS containing 2.5% non-fat dry milk, and the blots were incubated for two hours at room temperature with gentle shaking. The blots were then washed three times, 10 minutes each, in PBS, then quickly rinsed with $H_2O$. The blots were developed using commercially available chemiluminescent substrate reagents (SUPERSIGNAL ULTRA reagents 1 and 2 mixed 1:1; reagents obtained from Pierce Chemical Co.), and the signal was captured using image analysis software (LUMI-IMAGER Lumi Analyst 3.0; Boehringer Mannheim GmbH, Germany) for times ranging from 10 seconds to 5 minutes or as necessary.

The purified zvefg4-nee-GFD appeared as two bands on the silver-stained gel at about 31 and 17 kDa under non-reducing conditions and as a single band of 17 kDa under reducing conditions. This suggested existence of a dimeric form of zvegf4-nee-GFD under non-reducing conditions. The purified protein consisted of approximately 90% dimer and 10% monomer.

Example 8

Recombinant human zvegf4 (expressed from the full-length coding sequence) was analyzed for mitogenic activity on rat liver stellate cells (Greenwel et al., *Laboratory Invest.* 65:644, 1991; Greenwel et al., *Laboratory Invest.* 69:210, 1993), human aortic smooth muscle cells (Clonetics Corp., Walkersville, Md.), human retinal pericytes (Clonetics Corp.) and human hepatic fibroblasts (Clonetics Corp.). Test samples consisted of conditioned media (CM) from adenovirally infected HaCaT human keratinocyte cells (Boukamp et al., *J. Cell. Biol.* 106:761-771, 1988; Skobe and Fusenig, *Proc. Natl. Acad. Sci. USA* 95:1050-1055, 1998; obtained from Dr. Norbert E. Fusenig, Deutsches Krebsforschungszentrum, Heidelberg, Germany) expressing full length zvegf4. Control CM was generated from HaCaT cells infected with a parental GFP-expressing adenovirus (zPar). The CM were concentrated 10-fold using a 15-ml centrifugal filter device with a 10K membrane filter (ULTRAFREE; Millipore Corp., Bedford, Mass.), then diluted back to 1× with ITS medium (serum-free DMEM/Ham's F-12 medium containing 5 µg/ml insulin, 20 µg/ml transferrin, and 16 pg/ml selenium). Cells were plated at a density of 2,000 cells/well in 96-well culture plates and grown for approximately 72 hours in DMEM containing 10% fetal calf serum at 37° C. Cells were quiesced by incubating them for approximately 20 hours in ITS medium. At the time of the assay, the medium was removed, and test samples were added to the wells in triplicate. For measurement of [$^3$H]thymidine incorporation, 20 µl of a 50 µCi/ml stock in DMEM was added directly to the cells, for a final activity of 1 µCi/well. After another 24-hour incubation, media were removed and cells were incubated with 0.1 ml of trypsin until cells detached. Cells were harvested onto 96-well filter plates using a sample harvester (FILTERMATE harvester; Packard Instrument Co., Meriden, Conn.). The plates were then dried at 65° C. for 15 minutes, sealed after adding 40 µl/well scintillation cocktail (MICROSCINT 0; Packard Instrument Co.) and counted on a microplate scintillation counter (TOPCOUNT; Packard Instrument Co.). Results, presented in Table 2, demonstrated that zvegf4 CM had approximately 7-fold higher mitogenic activity than control CM on pericytes cells and approximately a 1.5-2.4-fold higher mitogenic activity on the other cell types tested. While not wishing to be bound by theory, it is believed that the observed activity may be due to the presence of cleaved zvegf4 protein (i.e., growth factor domain).

TABLE 2

| | CPM incorporated | | | |
| | Zvegf4 (1 × CM) | | zPar (1 × CM) | |
| Sample | Mean | St. dev. | Mean | St. dev. |
|---|---|---|---|---|
| Human retinal pericytes | 3621 | 223 | 523 | 306 |
| Human hepatic fibroblasts | 7757 | 753 | 3232 | 264 |
| Human aortic SMC | 2009 | 37 | 1263 | 51 |
| Rat liver stellate cells | 34707 | 1411 | 14413 | 1939 |

Example 9

Recombinant, C-terminally glu-glu tagged, human zvegf4 (expressed in baculovirus-infected cells expressing a full-length zvegf4 coding sequence) was analyzed for mitogenic activity on human aortic smooth muscle cells (HAoSMC) (Clonetics), human retinal pericytes (Clonetics) and human aortic adventitial fibroblasts (AoAF) (Clonetics). Cells were plated at a density of 2,000 cells/well in 96-well culture plates and grown for approximately 72 hours in DMEM containing 10% fetal calf serum at 37° C. Cells were quiesced by incubating them for 20 hours in ITS medium. At the time of the assay, the medium was removed, and test samples were added to the wells in triplicate. Purified protein in a buffer containing 0.1% BSA was serially diluted into ITS medium at concentrations of 1 µg/ml to 1 ng/ml and added to the test plate. A control buffer of 0.1% BSA was diluted identically to the highest concentration of zvegf4 protein and added to the plate. For measurement of [$^3$H]thymidine incorporation, 20 µl of a 50 µCi/ml stock in DMEM was added directly to the cells, for a final activity of 1 µCi/well. After another 24-hour incubation, mitogenic activity was assessed by measuring the uptake of [$^3$H]thymidine. Media were removed, and cells were incubated with 0.1 ml of trypsin until cells detached. Cells were harvested onto 96-well filter plates using a sample harvester (FILTERMATE harvester; Packard Instrument Co., Meriden, Conn.). The plates were then dried at 65° C. for 15 minutes, sealed after adding 40 µl/well scintillation cocktail (MICROSCINT O; Packard Instrument Co.) and counted on a microplate scintillation counter (TOPCOUNT; Packard Instrument Co.). Results, presented in Table 3, demonstrated that 80 ng/ml zvegf4 had approximately 1.7-fold higher mitogenic activity on pericytes, 3.2-fold higher activity on aortic SMCs, and 2.6-fold higher activity on aortic fibroblasts as compared to the buffer control.

TABLE 3

| | CPM Incorporated | | | | | |
|---|---|---|---|---|---|---|
| | Pericytes | | HAoSMC | | AoAF | |
| Sample | Mean | St. dev. | Mean | St. dev. | Mean | St. dev. |
| Zvegf4, 80 ng/ml | 96.7 | 18.2 | 488.7 | 29.6 | 177.0 | 1.0 |
| Zvegf4, 20 ng/ml | 81.7 | 11.7 | 211.7 | 50.8 | 107.7 | 20.1 |
| Zvegf4, 5 ng/ml | 67.3 | 6.7 | 191.7 | 4.5 | 123.7 | 10.5 |
| Buffer control | 58.7 | 8.5 | 152.3 | 40.1 | 68.7 | 8.3 |

Example 10

The protein-coding region of human zvegf4 DNA was amplified by PCR using primers that added PmeI and AscI restriction sites at the 5' and 3' termini, respectively. The resulting zvegf4 cDNA was cloned into the EcoRV-AscI sites of pZyTrack (Example 4). Recombinant adenovirus was generated in 293A cells and purified on CsCl gradients. Viral particle numbers were determined by spectrophotometry, and infectious particle numbers were determined by $TCID_{50}$ assay. The virus was designated AdZyvegf4.

Eight-week-old C57BL/6 mice were infected with AdZyvegf4 to determine the effects on serum chemistry, complete blood counts (CBC), body and organ weight changes, and histology. On day −1, the mice were tagged, individually weighed, and group normalized for separation into treatment groups (4 mice per cage). Group 1 mice (n=8 females, 7 males) received GFP (control) adenovirus, $1 \times 10^{11}$ particles. Group 2 mice (n=8 females, 6 males) received zvegf4 adenovirus, $1 \times 10^{11}$ particles. Group 3 mice (n=8 females, 8 males) were untreated controls. On day 0, the mice received injections of the appropriate adenovirus solution. On day 10, blood was collected (under ether anesthesia) for CBCs and clinical chemistry measurements. On day 20, mice were weighed and sacrificed by cervical dislocation after collecting blood (under ether anesthesia) for CBCs and clinical chemistry measurements. Selected tissues were fixed and evaluated for morphological changes. The following pathological findings were noted in the majority (80-100%) of the animals treated with the AdZyvegf4 adenovirus, and were not observed in either of the other two groups.

In the liver, there was moderate proliferation of sinusoidal cells, especially cells with small ovoid nuclei and no observable cytoplasm lining the sinusoids that were more clustered in the venous regions of the hepatic lobule. The cells appeared to be spindle Ito (or stellate) cells, which are a major cell type incriminated in the onset and progression of hepatic fibrosis.

In all AdZyvegf4-treated animals, the glomeruli of the kidneys were enlarged and were characterized by increased cellularity, diagnosed as proliferative glomerulopathy. Because of their location and morphological characteristics, the proliferating cells within the glomerulus that contributed to its enlargement were most likely mesangial cells. In addition, there was evidence of tubular regeneration in many of the kidneys, characterized by tubular epithelial cells with increased basophilia.

An increased amount of bronchoalveolar lymphoid tissue was noted in the lungs of the AdZyvegf4-treated animals. Bronchoalveolar lymphoid tissue consisted predominantly of clusters of lymphocytes admixed with fewer numbers of plasma cells around vessels within the lung parenchyma, a sign of lung inflammatory response, which is an important initiator and participant in several forms of lung fibrosis.

In the femur, the majority of animals displayed minimal to severe endosteal bone filling the marrow space, with decreased amounts of hematopoietic elements resulting from loss of marrow space due to the proliferating endosteal bone. In addition, four of six male and two of eight female animals had proliferation of stromal cells, which was characterized by an increased number of spindle-shaped cells.

Example 11

90 µg of full-length, recombinant human zvegf4 protein was dissolved in 500 µl PBS containing 2 mCi $Na^{125}I$ (Amersham Corp.). One derivatized, nonporous polystyrene bead (IODO-BEADS; Pierce, Rockford, Ill.) was added, and the reaction mixture was incubated one minute on ice. The iodinated protein was separated from unincorporated $^{125}I$ by gel filtration using an elution buffer of 10% acetic acid, 150 mM NaCl, and 0.25% gelatin. The active fraction contained 29 µg/ml $^{125}I$-zvegf4 with a specific activity of $3.0 \times 10^4$ cpm/ng.

The following cell lines were plated into the wells of a 24-well tissue culture dish and cultured in growth medium for three days:
1. Human retinal pericytes, passage 6 (pericytes).
2. Rat stellate cells, passage 8.
3. Human umbilical vein endothelial cells, passage 4 (HUVEC).
4. Human aortic adventitial fibroblasts, passage 5 (AoAF).
5. Human aortic smooth muscle cells, passage 2 (AoSMC).

Cells were washed once with ice-cold binding buffer (HAM'S F-12 containing 2.5 mg/ml BSA, 20 mM HEPES, pH 7.2), then 250 µl of the following solutions was added to each of three wells of the culture dishes containing the test cells. Binding solutions were prepared in 5 mL of binding buffer with 250 pM $^{125}I$-zvegf4 and:
1. No addition.
2. 25 nM zvegf4.
3. 25 nM zvegf3 (PDGF-C).
4. 25 nM PDGF-AA.
5. 25 nM PDGF-BB.

The reaction mixtures were incubated on ice for 2 hours, then washed three times with one ml of ice-cold binding buffer. The bound $^{125}I$-zvegf4 was quantitated by gamma counting a t-octylphenoxypolyethoxyethanol (TRITON X-100) extract of the cells.

Results, shown in Table 4, indicate binding of zvegf4 to pericytes, stellate cells, AoAF, and AoSMC, but not to HUVEC. The first column represents total CPM $^{125}I$-zvegf4 bound/well. The second column is $^{125}I$-zvegf4 bound/well when blocked with cold ligand. The difference between the two numbers represents specific binding.

TABLE 4

| Cell Type | $^{125}I$-zvegf4 Bound (CPM) | $^{125}I$-zvegf4 Bound w/cold zvegf4 (CPM) |
|---|---|---|
| 1. Pericytes | 3083 +/− 864 | 623 +/− 60 |
| 2. Stellate Cells | 2131 +/− 450 | 413 +/− 164 |
| 3. HUVEC | 485 +/− 91 | 227 +/− 13 |
| 4. AoAF | 1544 +/− 131 | 300 +/− 15 |
| 5. AoSMC | 1628 +/− 203 | 440 +/− 46 |

Zvegf4 binding was not significantly reduced by PDGF-AA or PDGF-BB (data not shown). These results indicate that full-length zvegf4 can bind to the tested cells at binding sites distinct from those for the AA and BB isoforms of PDGF. These zvegf4 binding sites may be either (1) sites on known PDGF receptors that are distinct from the binding sites for the AA and BB isoforms, or (2) one or more different molecules, such as cell-surface semaphorins.

Example 12

The activity of recombinant human zvegf4 growth factor domain was tested on BHK cell lines that stably expressed the α subunit of the PDGF receptor, the β subunit of the PDGF receptor, or both the α and β subunits of the PDGF receptor. Wild-type BHK 570 cells (which do not respond to PDGF because they do not express adequate levels of PDGF receptors) and stable BHK cell lines that expressed the human PDGF receptor subunits were plated at $10\text{-}15 \times 10^3$ cells/well in 96-well cell culture trays in DMEM (Life Technologies, Gaithersburg, Md.) supplemented with 10% fetal bovine serum (HyClone Laboratories, Inc., Logan, Utah). The medium of the stable clones was further supplemented with 200 nM methotrexate to maintain stable selection. At 70-80% confluence (the next day), the growth medium was replaced with serum-free medium, and the cells were infected with an adenoviral reporter construct (designated KZ 136) containing a firefly luciferase gene under the control of an SRE-STAT promoter at 1,000:1 multiplicity of infection (1,000 viral particles per cell). Twenty-four hours later, the medium was once more replaced with serum-free medium, and recombinant human zvegf4 growth factor domain was added to the cells. Four hours later, the cells were lysed, and the luciferase activity in the lysate was determined using a commercially available kit (obtained from Promega Corporation, Madison, Wis.) and a luminometer device (LUMINOSKAN; Labsystems Oy, Helsinki, FI) to detect the emitted luminescence. As shown in Tables 5-7, zvegf4 triggered responses in all three receptor-expressing BHK cell lines (but not in wild-type BHK cells, not shown), indicating that it can signal through αα, ββ and αβ PDGF receptor complexes.

TABLE 5

BHK expressing the PDGF receptor alpha subunit

| Zvegf4 (ng/ml) | Luciferase Units |
|---|---|
| 0 | 2.14 |
| 0.3 | 2.12 |
| 1 | 2.92 |
| 3 | 4.50 |
| 10 | 9.60 |
| 30 | 13.30 |
| 100 | 21.95 |

TABLE 6

BHK expressing PDGF receptor beta subunit

| Zvegf4 (ng/ml) | Luciferase Units |
|---|---|
| 0 | 4.49 |
| 0.3 | 8.53 |
| 1 | 14.77 |
| 3 | 20.91 |
| 10 | 37.22 |
| 30 | 40.16 |
| 100 | 36.41 |

TABLE 7

BHK cells expressing PDGF receptor alpha and beta subunits

| Zvegf4 (ng/ml) | Luciferase Units |
|---|---|
| 0 | 6.64 |
| 0.3 | 13.99 |
| 1 | 19.11 |
| 3 | 26.21 |
| 10 | 44.25 |
| 30 | 61.15 |
| 100 | 60.25 |

Example 13

Human aortic smooth muscle cells at passage 6 (Clonetics) were plated at $10 \times 10^3$ cells/well in 96-well cell culture trays in DMEM supplemented with 10% fetal bovine serum. At confluence (the next day), the growth medium was replaced with serum-free DMEM containing 0.1% BSA, and the cells were returned to the incubator, allowing for partial growth arrest. Twenty-four hours later, the media were once more replaced with serum-free medium with BSA. Recombinant human zvegf4 growth factor domain (30 ng/ml final concentration in the well) was mixed with neutralizing monoclonal antibodies against the alpha or beta PDGF receptor subunits or with non-immune mouse IgG (20 µg/ml final concentration in the well) for 10 minutes at room temperature. The mixture was then added to the cells. [$^3$H]-thymidine at 1 µCi/ml (Amersham, final concentration in the well) was added immediately afterwards, and the cells were returned to the incubator for an additional 24 hours to allow for [$^3$H]-thymidine incorporation into newly synthesized DNA. The cells were washed twice to remove unincorporated label and were harvested using a sample harvester (FILTERMATE 196 harvester; Packard Instrument Co.). Incorporated thymidine was determined using a scintillation counter (TOPCOUNT; Packard Instrument Co.). Results from triplicate well determinations, expressed as mean±standard deviation of cpm of radioactivity per well, are shown in Table 8. "Response" indicates the fold increase in thymidine incorporation resulting from the addition of zvegf4. The data show that the response of human aortic smooth muscle cells to zvegf4 was substantially reduced by both anti-alpha and anti-beta PDGF receptor subunit neutralizing antibodies, indicating that both PDGF receptor subunits are bound by zvegf4.

TABLE 8

| Antibody | zvegf4 | [$^3$H]-Thymidine (cpm) | Response |
|---|---|---|---|
| Non-immune serum (Control) | − | 81 ± 21 | |
| Non-immune serum (Control) | + | 696 ± 60 | 8-fold |
| anti-PDGF-Rβ | − | 116 ± 19 | |
| anti-PDGF-Rβ | + | 151 ± 15 | 1.4-fold |
| anti-PDGF-Rα | − | 102 ± 32 | |
| anti-PDGF-Rα | + | 322 ± 64 | 3.2-fold |

Example 14

Rat stellate cells were grown in 48-well tissue clusters (FALCON; BD Labware, Bedford, Mass.) in DMEM (Life Technologies, Inc.) supplemented with 10% fetal bovine serum (Hyclone Laboratories, Inc.). At 80% confluence, the cells were switched to growth-arrest medium by substituting 0.1% BSA (Sigma-Aldrich Corp., St. Louis, Mo.) for serum. Two days later the growth-arrest medium was replaced with the same medium, and recombinant human zvegf4 growth factor domain was added to the cells. After 48 hours, the conditioned media were collected, and TGF-β1 levels were determined using an ELISA kit (obtained from R&D Systems, Minneapolis, Minn.). Results are shown in Table 9.

TABLE 9

| Treatment | pg TGF-β1 per well |
| --- | --- |
| BSA Control | 2 ± 3 |
| Zvegf4 3 ng/ml | 32 ± 28 |
| Zvegf4 30 ng/ml | 120 ± 12 |
| Zvegf4 300 ng/ml | 175 ± 71 |

Example 15

OC10B mouse osteoblasts (Thomson et al., *J. Bone Min. Res.*, 13(2):195-204, 1998) were grown in 96-well tissue clusters (FALCON) until confluence in DMEM (Life Technologies, Inc.) supplemented with 10% fetal bovine serum (Hyclone Laboratories, Inc.). They were then switched to growth-arrest medium by substituting 0.1% BSA (Sigma-Aldrich Corp.) for serum. Forty-eight hours later, the growth-arrest medium was replaced with the same medium, and recombinant human zvegf4 growth factor domain was added to the cells. The cells were pulsed with 1 µCi/ml [$^3$H]-thymidine (NEN Life Science Products, Inc., Boston, Mass.) for 8 hours, 16-24 hours after addition of zvegf4. The radioactivity incorporated by the cells was determined by harvesting the cells with a sample harvester and counting the incorporated label using a microplate scintillation counter.

Results, shown in Table 10, indicate that zvegf4 directly stimulates osteoblast proliferation. Zvegf4 antagonists may therefore be useful in reducing growth of osteoblasts, such as in osteosarcomas or osteoblastic prostate metastases.

TABLE 10

| Treatment | cpm/well ($10^{-3}$) |
| --- | --- |
| BSA Control | 17 ± 2 |
| Zvegf4 1 ng/ml | 36 ± 11 |
| Zvegf4 3 ng/ml | 42 ± 8 |
| Zvegf4 10 ng/ml | 51 ± 17 |
| Zvegf4 30 ng/ml | 59 ± 11 |
| Zvegf4 100 ng/ml | 51 ± 25 |
| Zvegf4 300 ng/ml | 63 ± 13 |

Example 16

OC10B cells in vitro can differentiate into both osteoblasts and adipocytes (fat cells) when grown in a medium containing 100 µg/ml ascorbic acid and 10 mM beta-glycerophosphate (Thomson et al., ibid.). This differentiation recapitulates the in vivo physiological process whereby both cell lineages are derived from a common, bi-potential progenitor.

OC10B cells were cultured in the presence of ascorbic acid and beta-glycerophosphate for 10 days. Zvegf4 suppressed differentiation of the cells into adipocytes, as determined by the absence of cells containing light-reflective fat droplets. In contrast, there was an increase in the number and size of mineralized foci as assessed by Von Kossa staining.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A method of treating a fibroproliferative disorder of heart or lung in a mammal comprising administering to the mammal a composition comprising a therapeutically effective amount of a zvegf4 antagonist in combination with a pharmaceutically acceptable delivery vehicle, wherein the zvegf4 antagonist is a monoclonal anti-zvegf4 antibody that binds to an epitope of a protein as shown in SEQ ID NO: 2 from amino acid residue 258 to amino acid residue 370.

2. The method of claim 1, wherein the fibroproliferative disorder is a fibroproliferative disorder of heart.

3. The method of claim 1, wherein the fibroproliferative disorder is a fibroproliferative disorder of lung.

4. The method of claim 1, wherein the antibody is a humanized antibody.

5. The method of claim 1, wherein the antibody is a single-chain antibody.

6. The method of claim 1, wherein the antibody is an antigen binding fragment selected from the group consisting of a F(ab')2 fragment and a Fab fragment.

* * * * *

SEQUENCE LISTING

```
<160> NUMBER OF SEQ ID NOS: 13

<210> SEQ ID NO 1
<211> LENGTH: 1882
<212> TYPE: DNA
<213> ORGANISM: Homo sapiens
<220> FEATURE:
<221> NAME/KEY: CDS
<222> LOCATION: (226)...(1338)

<400> SEQUENCE: 1
ccgtcaccat ttatcagctc agcaccacaa ggaagtgcgg cacccacacg cgctcggaaa        60
gttcagcatg caggaagttt ggggagagct cggcgattag cacagcgacc cgggccagcg       120
cagggcgagc gcaggcggcg agagcgcagg gcggcgcggc gtcggtcccg ggagcagaac       180
ccggcttttt cttggagcga cgctgtctct agtcgctgat cccaa atg cac cgg ctc       237
                                                  Met His Arg Leu
                                                   1 atc ttt gtc tac act cta atc tgc gca aac ttt tgc agc tgt cgg gac         285
Ile Phe Val Tyr Thr Leu Ile Cys Ala Asn Phe Cys Ser Cys Arg Asp
  5                  10                  15                  20 act tct gca acc ccg cag agc gca tcc atc aaa gct ttg cgc aac gcc         333
Thr Ser Ala Thr Pro Gln Ser Ala Ser Ile Lys Ala Leu Arg Asn Ala
                 25                  30                  35 aac ctc agg cga gat gag agc aat cac ctc aca gac ttg tac cga aga         381
Asn Leu Arg Arg Asp Glu Ser Asn His Leu Thr Asp Leu Tyr Arg Arg
```

```
                40                  45                  50
gat gag acc atc cag gtg aaa gga aac ggc tac gtg cag agt cct aga    429
Asp Glu Thr Ile Gln Val Lys Gly Asn Gly Tyr Val Gln Ser Pro Arg
         55                  60                  65 ttc ccg aac agc tac ccc agg aac ctg ctc ctg aca tgg cgg ctt cac    477
Phe Pro Asn Ser Tyr Pro Arg Asn Leu Leu Leu Thr Trp Arg Leu His
 70                  75                  80 tct cag gag aat aca cgg ata cag cta gtg ttt gac aat cag ttt gga    525
Ser Gln Glu Asn Thr Arg Ile Gln Leu Val Phe Asp Asn Gln Phe Gly
 85                  90                  95                 100 tta gag gaa gca gaa aat gat atc tgt agg tat gat ttt gtg gaa gtt    573
Leu Glu Glu Ala Glu Asn Asp Ile Cys Arg Tyr Asp Phe Val Glu Val
                105                 110                 115 gaa gat ata tcc gaa acc agt acc att att aga gga cga tgg tgt gga    621
Glu Asp Ile Ser Glu Thr Ser Thr Ile Ile Arg Gly Arg Trp Cys Gly
             120                 125                 130 cac aag gaa gtt cct cca agg ata aaa tca aga acg aac caa att aaa    669
His Lys Glu Val Pro Pro Arg Ile Lys Ser Arg Thr Asn Gln Ile Lys
             135                 140                 145 atc aca ttc aag tcc gat gac tac ttt gtg gct aaa cct gga ttc aag    717
Ile Thr Phe Lys Ser Asp Asp Tyr Phe Val Ala Lys Pro Gly Phe Lys
     150                 155                 160 att tat tat tct ttg ctg gaa gat ttc caa ccc gca gca gct tca gag    765
Ile Tyr Tyr Ser Leu Leu Glu Asp Phe Gln Pro Ala Ala Ala Ser Glu
165                 170                 175                 180 acc aac tgg gaa tct gtc aca agc tct att tca ggg gta tcc tat aac    813
Thr Asn Trp Glu Ser Val Thr Ser Ser Ile Ser Gly Val Ser Tyr Asn
                185                 190                 195 tct cca tca gta acg gat ccc act ctg att gcg gat gct ctg gac aaa    861
Ser Pro Ser Val Thr Asp Pro Thr Leu Ile Ala Asp Ala Leu Asp Lys
             200                 205                 210 aaa att gca gaa ttt gat aca gtg gaa gat ctg ctc aag tac ttc aat    909
Lys Ile Ala Glu Phe Asp Thr Val Glu Asp Leu Leu Lys Tyr Phe Asn
             215                 220                 225 cca gag tca tgg caa gaa gat ctt gag aat atg tat ctg gac acc cct    957
Pro Glu Ser Trp Gln Glu Asp Leu Glu Asn Met Tyr Leu Asp Thr Pro
     230                 235                 240 cgg tat cga ggc agg tca tac cat gac cgg aag tca aaa gtt gac ctg   1005
Arg Tyr Arg Gly Arg Ser Tyr His Asp Arg Lys Ser Lys Val Asp Leu
245                 250                 255                 260 gat agg ctc aat gat gat gcc aag cgt tac agt tgc act ccc agg aat   1053
Asp Arg Leu Asn Asp Asp Ala Lys Arg Tyr Ser Cys Thr Pro Arg Asn
                265                 270                 275 tac tcg gtc aat ata aga gaa gag ctg aag ttg gcc aat gtg gtc ttc   1101
Tyr Ser Val Asn Ile Arg Glu Glu Leu Lys Leu Ala Asn Val Val Phe
             280                 285                 290 ttt cca cgt tgc ctc ctc gtg cag cgc tgt gga gga aat tgt ggc tgt   1149
Phe Pro Arg Cys Leu Leu Val Gln Arg Cys Gly Gly Asn Cys Gly Cys
             295                 300                 305 gga act gtc aac tgg agg tcc tgc aca tgc aat tca ggg aaa acc gtg   1197
Gly Thr Val Asn Trp Arg Ser Cys Thr Cys Asn Ser Gly Lys Thr Val
     310                 315                 320 aaa aag tat cat gag gta tta cag ttt gag cct ggc cac atc aag agg   1245
Lys Lys Tyr His Glu Val Leu Gln Phe Glu Pro Gly His Ile Lys Arg
325                 330                 335                 340 agg ggt aga gct aag acc atg gct cta gtt gac atc cag ttg gat cac   1293
Arg Gly Arg Ala Lys Thr Met Ala Leu Val Asp Ile Gln Leu Asp His
                345                 350                 355 cat gaa cga tgc gat tgt atc tgc agc tca aga cca cct cga taa       1338
His Glu Arg Cys Asp Cys Ile Cys Ser Ser Arg Pro Pro Arg *
```

-continued

```
                360                 365                 370
gagaatgtgc acatccttac attaagcctg aaagaacctt tagtttaagg agggtgagat   1398
aagagaccct tttcctacca gcaaccaaac ttactactag cctgcaatgc aatgaacaca   1458
agtggttgct gagtctcagc cttgctttgt taatgccatg gcaagtagaa aggtatatca   1518
tcaacttcta tacctaagaa tataggattg catttaataa tagtgtttga ggttatatat   1578
gcacaaacac acacagaaat atattcatgt ctatgtgtat atagatcaaa tgttttttt    1638 ttttggtata tataaccagg tacaccagag gttacatatg tttgagttag actcttaaaa   1698
tcctttgcca aaataaggga tggtcaaata tatgaaacat gtctttagaa aatttaggag   1758
ataaatttat ttttaaattt tgaaacacga aacaattttg aatcttgctc tcttaaagaa   1818
agcatcttgt atattaaaaa tcaaaagatg aggctttctt acatatacat cttagttgat   1878
tatt                                                                1882
```

<210> SEQ ID NO 2
<211> LENGTH: 370
<212> TYPE: PRT
<213> ORGANISM: Homo sapiens

<400> SEQUENCE: 2

```
Met His Arg Leu Ile Phe Val Tyr Thr Leu Ile Cys Ala Asn Phe Cys
 1               5                   10                  15

Ser Cys Arg Asp Thr Ser Ala Thr Pro Gln Ser Ala Ser Ile Lys Ala
             20                  25                  30

Leu Arg Asn Ala Asn Leu Arg Arg Asp Glu Ser Asn His Leu Thr Asp
         35                  40                  45

Leu Tyr Arg Arg Asp Glu Thr Ile Gln Val Lys Gly Asn Gly Tyr Val
     50                  55                  60

Gln Ser Pro Arg Phe Pro Asn Ser Tyr Pro Arg Asn Leu Leu Leu Thr
 65                  70                  75                  80

Trp Arg Leu His Ser Gln Glu Asn Thr Arg Ile Gln Leu Val Phe Asp
                 85                  90                  95

Asn Gln Phe Gly Leu Glu Glu Ala Glu Asn Asp Ile Cys Arg Tyr Asp
            100                 105                 110

Phe Val Glu Val Glu Asp Ile Ser Glu Thr Ser Thr Ile Ile Arg Gly
        115                 120                 125

Arg Trp Cys Gly His Lys Glu Val Pro Pro Arg Ile Lys Ser Arg Thr
    130                 135                 140

Asn Gln Ile Lys Ile Thr Phe Lys Ser Asp Asp Tyr Phe Val Ala Lys
145                 150                 155                 160

Pro Gly Phe Lys Ile Tyr Tyr Ser Leu Leu Glu Asp Phe Gln Pro Ala
                165                 170                 175

Ala Ala Ser Glu Thr Asn Trp Glu Ser Val Thr Ser Ser Ile Ser Gly
            180                 185                 190

Val Ser Tyr Asn Ser Pro Ser Val Thr Asp Pro Thr Leu Ile Ala Asp
        195                 200                 205

Ala Leu Asp Lys Lys Ile Ala Glu Phe Asp Thr Val Glu Asp Leu Leu
    210                 215                 220

Lys Tyr Phe Asn Pro Glu Ser Trp Gln Glu Asp Leu Glu Asn Met Tyr
225                 230                 235                 240

Leu Asp Thr Pro Arg Tyr Arg Gly Arg Ser Tyr His Asp Arg Lys Ser
                245                 250                 255

Lys Val Asp Leu Asp Arg Leu Asn Asp Asp Ala Lys Arg Tyr Ser Cys
            260                 265                 270
```

-continued

```
Thr Pro Arg Asn Tyr Ser Val Asn Ile Arg Glu Glu Leu Lys Leu Ala
        275                 280                 285
Asn Val Val Phe Phe Pro Arg Cys Leu Leu Val Gln Arg Cys Gly Gly
        290                 295                 300
Asn Cys Gly Cys Gly Thr Val Asn Trp Arg Ser Cys Thr Cys Asn Ser
305                 310                 315                 320
Gly Lys Thr Val Lys Lys Tyr His Glu Val Leu Gln Phe Glu Pro Gly
                325                 330                 335
His Ile Lys Arg Arg Gly Arg Ala Lys Thr Met Ala Leu Val Asp Ile
                340                 345                 350
Gln Leu Asp His His Glu Arg Cys Asp Cys Ile Cys Ser Ser Arg Pro
        355                 360                 365
Pro Arg
    370

<210> SEQ ID NO 3
<211> LENGTH: 1472
<212> TYPE: DNA
<213> ORGANISM: Mus musculus
<220> FEATURE:
<221> NAME/KEY: CDS
<222> LOCATION: (93)...(1205)

<400> SEQUENCE: 3
agggactgtg cagtagaaat ccgccgactc aacccttttgg gctttatttta tttacttttg    60 gagcaacgcg atccctaggt cgctgagccc aa atg caa cgg ctc gtt tta gtc   113
                                   Met Gln Arg Leu Val Leu Val
                                     1               5 tcc att ctc ctg tgc gcg aac ttt agc tgc tat ccg gac act ttt gcg   161
Ser Ile Leu Leu Cys Ala Asn Phe Ser Cys Tyr Pro Asp Thr Phe Ala
         10                  15                  20 act ccg cag aga gca tcc atc aaa gct ttg cgc aat gcc aac ctc agg   209
Thr Pro Gln Arg Ala Ser Ile Lys Ala Leu Arg Asn Ala Asn Leu Arg
     25                  30                  35 aga gat gag agc aat cac ctc aca gac ttg tac cag aga gag gag aac   257
Arg Asp Glu Ser Asn His Leu Thr Asp Leu Tyr Gln Arg Glu Glu Asn
 40                  45                  50                  55 att cag gtg aca agc aat ggc cat gtg cag agt cct cgc ttc ccg aac   305
Ile Gln Val Thr Ser Asn Gly His Val Gln Ser Pro Arg Phe Pro Asn
             60                  65                  70 agc tac cca agg aac ctg ctt ctg aca tgg tgg ctc cgt tcc cag gag   353
Ser Tyr Pro Arg Asn Leu Leu Leu Thr Trp Trp Leu Arg Ser Gln Glu
         75                  80                  85 aaa aca cgg ata caa ctg tcc ttt gac cat caa ttc gga cta gag gaa   401
Lys Thr Arg Ile Gln Leu Ser Phe Asp His Gln Phe Gly Leu Glu Glu
     90                  95                 100 gca gaa aat gac att tgt agg tat gac ttt gtg gaa gtt gaa gaa gtc   449
Ala Glu Asn Asp Ile Cys Arg Tyr Asp Phe Val Glu Val Glu Glu Val
105                 110                 115 tca gag agc agc act gtt gtc aga gga aga tgg tgt ggc cac aag gag   497
Ser Glu Ser Ser Thr Val Val Arg Gly Arg Trp Cys Gly His Lys Glu
120                 125                 130                 135 atc cct cca agg ata acg tca aga aca aac cag att aaa atc aca ttt   545
Ile Pro Pro Arg Ile Thr Ser Arg Thr Asn Gln Ile Lys Ile Thr Phe
            140                 145                 150 aag tct gat gac tac ttt gtg gca aaa cct gga ttc aag att tat tat   593
Lys Ser Asp Asp Tyr Phe Val Ala Lys Pro Gly Phe Lys Ile Tyr Tyr
        155                 160                 165 tca ttt gtg gaa gat ttc caa ccg gaa gca gcc tca gag acc aac tgg   641
```

```
Ser Phe Val Glu Asp Phe Gln Pro Glu Ala Ala Ser Glu Thr Asn Trp
        170                 175                 180 gaa tca gtc aca agc tct ttc tct ggg gtg tcc tat cac tct cca tca      689
Glu Ser Val Thr Ser Ser Phe Ser Gly Val Ser Tyr His Ser Pro Ser
185                 190                 195 ata acg gac ccc act ctc act gct gat gcc ctg gac aaa act gtc gca      737
Ile Thr Asp Pro Thr Leu Thr Ala Asp Ala Leu Asp Lys Thr Val Ala
200                 205                 210                 215 gaa ttc gat acc gtg gaa gat cta ctt aag cac ttc aat cca gtg tct      785
Glu Phe Asp Thr Val Glu Asp Leu Leu Lys His Phe Asn Pro Val Ser
                    220                 225                 230 tgg caa gat gat ctg gag aat ttg tat ctg gac acc cct cat tat aga      833
Trp Gln Asp Asp Leu Glu Asn Leu Tyr Leu Asp Thr Pro His Tyr Arg
                235                 240                 245 ggc agg tca tac cat gat cgg aag tcc aaa gtg gac ctg gac agg ctc      881
Gly Arg Ser Tyr His Asp Arg Lys Ser Lys Val Asp Leu Asp Arg Leu
            250                 255                 260 aat gat gat gtc aag cgt tac agt tgc act ccc agg aat cac tct gtg      929
Asn Asp Asp Val Lys Arg Tyr Ser Cys Thr Pro Arg Asn His Ser Val
265                 270                 275 aac ctc agg gag gag ctg aag ctg acc aat gca gtc ttc ttc cca cga      977
Asn Leu Arg Glu Glu Leu Lys Leu Thr Asn Ala Val Phe Phe Pro Arg
280                 285                 290                 295 tgc ctc ctc gtg cag cgc tgt ggt ggc aac tgt ggt tgc gga act gtc     1025
Cys Leu Leu Val Gln Arg Cys Gly Gly Asn Cys Gly Cys Gly Thr Val
                    300                 305                 310 aac tgg aag tcc tgc aca tgc agc tca ggg aag aca gtg aag aag tat     1073
Asn Trp Lys Ser Cys Thr Cys Ser Ser Gly Lys Thr Val Lys Lys Tyr
                315                 320                 325 cat gag gta ttg aag ttt gag cct gga cat ttc aag aga agg ggc aaa     1121
His Glu Val Leu Lys Phe Glu Pro Gly His Phe Lys Arg Arg Gly Lys
            330                 335                 340 gct aag aat atg gct ctt gtt gat atc cag ctg gat cat cat gag cga     1169
Ala Lys Asn Met Ala Leu Val Asp Ile Gln Leu Asp His His Glu Arg
345                 350                 355 tgt gac tgt atc tgc agc tca aga cca cct cga taa aacactatgc          1215
Cys Asp Cys Ile Cys Ser Ser Arg Pro Pro Arg *
360                 365                 370 acatctgtac tttgattatg aaaggacctt taggttacaa aaaccctaag aagcttctaa   1275
tctcagtgca atgaatgcat atggaaatgt tgctttgtta gtgccatggc aagaagaagc   1335
aaatatcatt aatttctata tacataaaca taggaattca cttatcaata gtatgtgaag   1395
atatgtatat atacttatat acatgactag ctctatgtat gtaaatagat taaatacttt   1455
attcagtata tttactg                                                  1472

<210> SEQ ID NO 4
<211> LENGTH: 370
<212> TYPE: PRT
<213> ORGANISM: Mus musculus

<400> SEQUENCE: 4

Met Gln Arg Leu Val Leu Val Ser Ile Leu Leu Cys Ala Asn Phe Ser
1               5                   10                  15

Cys Tyr Pro Asp Thr Phe Ala Thr Pro Gln Arg Ala Ser Ile Lys Ala
            20                  25                  30

Leu Arg Asn Ala Asn Leu Arg Arg Asp Glu Ser Asn His Leu Thr Asp
        35                  40                  45

Leu Tyr Gln Arg Glu Glu Asn Ile Gln Val Thr Ser Asn Gly His Val
    50                  55                  60
```

Gln Ser Pro Arg Phe Pro Asn Ser Tyr Pro Arg Asn Leu Leu Leu Thr
 65                  70                  75                  80

Trp Trp Leu Arg Ser Gln Glu Lys Thr Arg Ile Gln Leu Ser Phe Asp
             85                  90                  95

His Gln Phe Gly Leu Glu Glu Ala Glu Asn Asp Ile Cys Arg Tyr Asp
        100                 105                 110

Phe Val Glu Val Glu Glu Val Ser Glu Ser Ser Thr Val Val Arg Gly
            115                 120                 125

Arg Trp Cys Gly His Lys Glu Ile Pro Pro Arg Ile Thr Ser Arg Thr
        130                 135                 140

Asn Gln Ile Lys Ile Thr Phe Lys Ser Asp Asp Tyr Phe Val Ala Lys
145                 150                 155                 160

Pro Gly Phe Lys Ile Tyr Tyr Ser Phe Val Glu Asp Phe Gln Pro Glu
                165                 170                 175

Ala Ala Ser Glu Thr Asn Trp Glu Ser Val Thr Ser Ser Phe Ser Gly
            180                 185                 190

Val Ser Tyr His Ser Pro Ser Ile Thr Asp Pro Thr Leu Thr Ala Asp
        195                 200                 205

Ala Leu Asp Lys Thr Val Ala Glu Phe Asp Thr Val Glu Asp Leu Leu
    210                 215                 220

Lys His Phe Asn Pro Val Ser Trp Gln Asp Asp Leu Glu Asn Leu Tyr
225                 230                 235                 240

Leu Asp Thr Pro His Tyr Arg Gly Arg Ser Tyr His Asp Arg Lys Ser
                245                 250                 255

Lys Val Asp Leu Asp Arg Leu Asn Asp Asp Val Lys Arg Tyr Ser Cys
            260                 265                 270

Thr Pro Arg Asn His Ser Val Asn Leu Arg Glu Glu Leu Lys Leu Thr
        275                 280                 285

Asn Ala Val Phe Phe Pro Arg Cys Leu Leu Val Gln Arg Cys Gly Gly
    290                 295                 300

Asn Cys Gly Cys Gly Thr Val Asn Trp Lys Ser Cys Thr Cys Ser Ser
305                 310                 315                 320

Gly Lys Thr Val Lys Lys Tyr His Glu Val Leu Lys Phe Glu Pro Gly
                325                 330                 335

His Phe Lys Arg Arg Gly Lys Ala Lys Asn Met Ala Leu Val Asp Ile
            340                 345                 350

Gln Leu Asp His His Glu Arg Cys Asp Cys Ile Cys Ser Ser Arg Pro
        355                 360                 365

Pro Arg
    370

<210> SEQ ID NO 5
<211> LENGTH: 24
<212> TYPE: DNA
<213> ORGANISM: Artificial Sequence
<220> FEATURE:
<223> OTHER INFORMATION: oligonucleotide primer ZC21,987

<400> SEQUENCE: 5
caacctgttg tttgtcccgt cacc                                         24

<210> SEQ ID NO 6
<211> LENGTH: 24
<212> TYPE: DNA
<213> ORGANISM: Artificial Sequence
<220> FEATURE:
<223> OTHER INFORMATION: oligonucleotide primer ZC21,120

```
<400> SEQUENCE: 6
tccagagcat ccgcaatcag agtg                                          24

<210> SEQ ID NO 7
<211> LENGTH: 25
<212> TYPE: DNA
<213> ORGANISM: Artificial Sequence
<220> FEATURE:
<223> OTHER INFORMATION: oligonucleotide primer ZC26317

<400> SEQUENCE: 7
atcacctcac agacttgtac cagag                                         25

<210> SEQ ID NO 8
<211> LENGTH: 25
<212> TYPE: DNA
<213> ORGANISM: Artificial Sequence
<220> FEATURE:
<223> OTHER INFORMATION: oligonucleotide primer ZC26318

<400> SEQUENCE: 8
cctacaaatg tcattttctg cttcc                                         25

<210> SEQ ID NO 9
<211> LENGTH: 18
<212> TYPE: PRT
<213> ORGANISM: Artificial Sequence
<220> FEATURE:
<223> OTHER INFORMATION: peptide

<400> SEQUENCE: 9

Cys Gly His Lys Glu Val Pro Pro Arg Ile Lys Ser Arg Thr Asn Gln
 1               5                  10                  15

Ile Lys

<210> SEQ ID NO 10
<211> LENGTH: 25
<212> TYPE: PRT
<213> ORGANISM: Artificial Sequence
<220> FEATURE:
<223> OTHER INFORMATION: peptide

<400> SEQUENCE: 10

Glu Ser Trp Gln Glu Asp Leu Glu Asn Met Tyr Leu Asp Thr Pro Arg
 1               5                  10                  15

Tyr Arg Gly Arg Ser Tyr His Asp Cys
                20                  25

<210> SEQ ID NO 11
<211> LENGTH: 24
<212> TYPE: PRT
<213> ORGANISM: Artificial Sequence
<220> FEATURE:
<223> OTHER INFORMATION: peptide

<400> SEQUENCE: 11

Cys Phe Glu Pro Gly His Ile Lys Arg Arg Gly Arg Ala Lys Thr Met
 1               5                  10                  15

Ala Leu Val Asp Ile Gln Leu Asp
                20

<210> SEQ ID NO 12
<211> LENGTH: 6
<212> TYPE: PRT
```

```
<213> ORGANISM: Artificial Sequence
<220> FEATURE:
<223> OTHER INFORMATION: peptide

<400> SEQUENCE: 12

Glu Tyr Met Pro Met Glu
 1               5

<210> SEQ ID NO 13
<211> LENGTH: 6
<212> TYPE: PRT
<213> ORGANISM: Artificial Sequence
<220> FEATURE:
<223> OTHER INFORMATION: peptide

<400> SEQUENCE: 13

Glu Tyr Met Pro Thr Asp
 1               5
```